US012690813B2

(12) United States Patent (10) Patent No.: US 12,690,813 B2
Shimuta et al. (45) Date of Patent: Jul. 28, 2026

(54) ORAL APPLIANCE

(71) Applicant: Murata Manufacturing Co., Ltd., Nagaokakyo (JP)

(72) Inventors: Toru Shimuta, Nagaokakyo (JP); Jun Takagi, Nagaokakyo (JP); Tomoki Takahashi, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 703 days.

(21) Appl. No.: 17/975,029

(22) Filed: Oct. 27, 2022

(65) Prior Publication Data

US 2023/0048975 A1 Feb. 16, 2023

Related U.S. Application Data

(63) Continuation of application No. PCT/JP2021/016299, filed on Apr. 22, 2021.

(30) Foreign Application Priority Data

Jun. 19, 2020 (JP) ................................. 2020-106459

(51) Int. Cl.
*A61B 5/00* (2006.01)
*A61N 5/06* (2006.01)
(52) U.S. Cl.
CPC ............ *A61B 5/682* (2013.01); *A61B 5/4542* (2013.01); *A61N 5/0603* (2013.01);
(Continued)
(58) Field of Classification Search
CPC ... A61B 5/682; A61B 5/4542; A61B 2562/08; A61B 5/01; A61B 5/082; A61B 5/228;
(Continued)

(56) References Cited

U.S. PATENT DOCUMENTS 11,529,093 B2 * 12/2022 Furukawa ............ A61B 5/4277
2002/0172917 A1 11/2002 Cao
(Continued)

FOREIGN PATENT DOCUMENTS

CN 107635459 A 1/2018
JP 2004170296 A 6/2004
(Continued)

OTHER PUBLICATIONS

KR-101865714-B1 Translation (Year: 2018).*
International Search Report in PCT/JP2021/016299, mailed Jun. 15, 2021, 3 pages.

*Primary Examiner* — Michael W Kahelin
*Assistant Examiner* — Attiya Sayyada Hussaini
(74) *Attorney, Agent, or Firm* — ArentFox Schiff LLP

(57) ABSTRACT

A sheet-shaped oral appliance is provided that is detachably attached to an oral body device and includes a functional portion with a sensor unit that acquires information in an oral cavity and an energy irradiation unit that radiates energy into the oral cavity, an electrical connection portion, and a wiring portion that connects at least one of the sensor unit and the energy irradiation unit to the electrical connection portion. The functional portion, the connection portion, and the wiring portion are formed by a wiring layer having first and second main surfaces that oppose each other, a first insulating layer arranged on the first main surface and a second insulating layer arranged on the second main surface. Moreover, in the functional portion, a thickness of the first insulating layer is smaller than a thickness of the second insulating layer.

20 Claims, 26 Drawing Sheets

(52) U.S. Cl.
CPC ... *A61B 2562/08* (2013.01); *A61N 2005/0606*
*(2013.01); *A61N 2005/0626* (2013.01)
(58) Field of Classification Search
CPC ... A61B 5/4277; A61B 5/4836; A61B 5/6844;
A61B 2560/0247; A61B 2560/0406;
A61B 2560/0443; A61B 2562/0214;
A61B 2562/14; A61B 5/14507; A61B
90/98; A61N 5/0603; A61N 2005/0606;
A61N 2005/0626; A61N 5/067; A61N
2005/0644
See application file for complete search history.

(56) References Cited

U.S. PATENT DOCUMENTS

| | | | |
|---|---|---|---|
| 2007/0295713 A1 * | 12/2007 | Carlton-Foss | G01K 1/16 |
| | | | 219/497 |
| 2016/0135728 A1 | 5/2016 | Furukawa et al. | |
| 2018/0020976 A1 | 1/2018 | Yossi | |
| 2020/0011827 A1 * | 1/2020 | Zhou | G01N 27/226 |
| 2020/0060550 A1 | 2/2020 | Pesach et al. | |

FOREIGN PATENT DOCUMENTS

| | | | |
|---|---|---|---|
| JP | 2009080091 A | | 4/2009 |
| JP | 2019033965 A | | 3/2019 |
| KR | 101865714 B1 * | | 7/2018 |
| WO | 2014041585 A1 | | 3/2014 |
| WO | 2015125222 A1 | | 8/2015 |

* cited by examiner

ORAL APPLIANCE

CROSS REFERENCE TO RELATED APPLICATIONS

This application is a continuation of PCT Application No. PCT/JP2021/016299, filed Apr. 22, 2021, which claims priority to Japanese Patent Application No. 2020-106459, filed Jun. 19, 2020, the entire contents of each of which are hereby incorporated by reference in their entirety.

TECHNICAL FIELD

The present invention relates to an oral appliance that is detachably attached to an oral body device.

BACKGROUND

International Publication No. 2015/125222 (hereinafter "Patent Document 1") discloses an intraoral moisture measuring device. The intraoral moisture measuring device described in Patent Document 1 includes a swing member, a moisture content detection unit provided at a tip of the swing member, and a biasing member for biasing the swing member in one direction of swing directions.

However, in recent years, there has been a demand for an oral appliance that is detachably attached to an oral body device and has improved performance.

SUMMARY OF THE INVENTION

Thus, according to an exemplary aspect, an oral appliance is provided that is sheet-shaped and detachably attached to an oral body device. The oral appliance includes a functional portion including at least one or a plurality of sensor units that acquires information in an oral cavity and one or a plurality of energy irradiation units that radiates energy into an oral cavity; a connection portion having an electrical connection portion; and a wiring portion including a wiring that connects at least one of sensor units and the plurality of energy irradiation units to the electrical connection portion. Moreover, the functional portion, the connection portion, and the wiring portion comprise a wiring layer having first and second main surfaces that oppose each other; and a plurality of insulating layers including a first insulating layer arranged on the first main surface of the wiring layer and a second insulating layer arranged on the second main surface of the wiring layer. Moreover, a thickness of the first insulating layer is smaller than a thickness of the second insulating layer in the functional portion.

According to the present invention, an oral appliance is provided that is detachably attached to an oral body device with improved performance.

DESCRIPTION OF EMBODIMENTS

Figure 1:
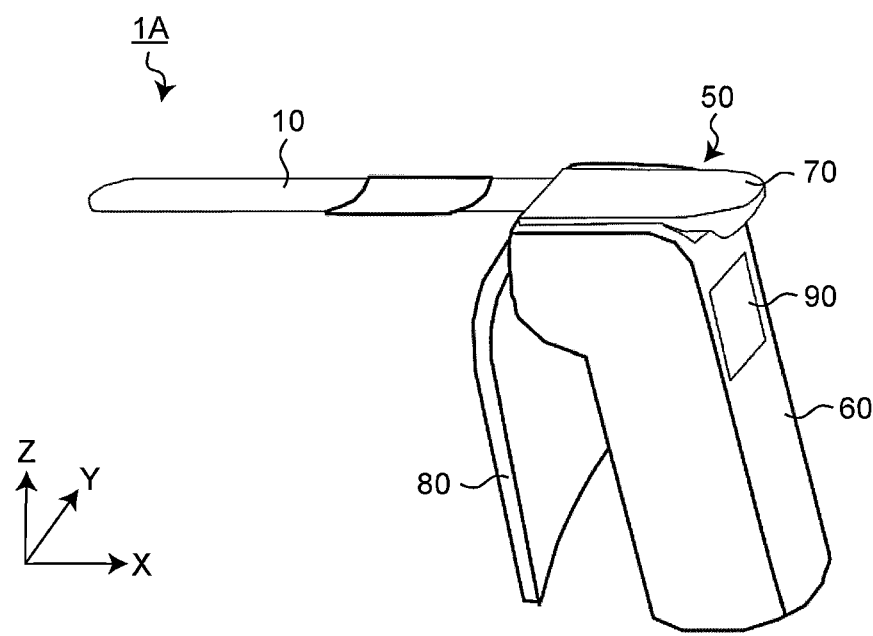
FIG. 1 is a schematic perspective view of an example of an oral device of Embodiment 1 according to an exemplary aspect.

In the moisture measuring device described in Patent Document 1, the moisture in an oral cavity is measured by bringing the moisture content detection unit (e.g., a sensor unit) provided on the tip side of the swing member, which swings with respect to a main body, into contact with a measurement site in the oral cavity. Further, in the moisture measuring device described in Patent Document 1, the sensor unit and the swing member are configured as a detachable portion (e.g., an oral appliance) that is detachable from the main body. As such, the sanitary state of the measuring device is maintained in a more appropriate state.

In such a device, since the sensor unit is covered with an insulator or the like, the sensor unit comes into contact with the measurement site via the insulator. Therefore, the sensitivity of the sensor unit may decrease due to the insulator, and it is difficult to improve a detection accuracy of the sensor unit. For this reason, the detection accuracy of the sensor unit needs to be improved.

In addition, an oral appliance including an energy irradiation unit that radiates energy, such as heat or light, into the oral cavity is also required to improve an energy irradiation efficiency.

Therefore, the present inventors have studied to solve the above-described problems by devising the thickness of an insulating layer covering a functional portion including at least one of a sensor unit and an energy irradiation unit, and arrived at the following invention.

In an exemplary aspect, an oral appliance is provided that is a sheet-shaped oral appliance detachably attached to an oral body device, and that includes a functional portion including at least one or a plurality of sensor units that acquires information in an oral cavity and one or a plurality of energy irradiation units that radiates energy into an oral cavity; a connection portion having an electrical connection portion; and a wiring portion including a wiring that connects at least one of the plurality of sensor units and the one or the plurality of energy irradiation units to the electrical connection portion. Moreover, the functional portion, the connection portion, and the wiring portion comprise a wiring layer having a first main surface and a second main surface on a side opposite to the first main surface; and a plurality of insulating layers including a first insulating layer arranged on the first main surface of the wiring layer and a second insulating layer arranged on the second main surface of the wiring layer. In addition, a thickness of the first insulating layer is smaller than a thickness of the second insulating layer in the functional portion. With such a configuration, the performance is improved in the oral appliance detachably attached to the oral body device.

In an exemplary aspect, the wiring layer and the plurality of insulating layers may be configured to be stacked. With such a configuration, the oral appliance is more easily inserted into the oral cavity.

In an exemplary aspect, a thickness of the wiring portion is larger than a thickness of the functional portion. With such a configuration, the mechanical strength of the wiring portion is improved.

In an exemplary aspect, the wiring portion has one or a plurality of shield layers arranged on the plurality of insulating layers. With such a configuration, noise generated from the wiring portion can be suppressed.

In an exemplary aspect, the wiring portion has a protective layer arranged on an outer periphery of the wiring portion. With such a configuration, a failure due to contact with the teeth or the like of a user can be suppressed when the oral appliance is used in the oral cavity.

In an exemplary aspect, the one or the plurality of sensor units has a sensor surface that acquires information on a measurement site in an oral cavity, and the sensor surface is arranged on the first main surface side of the wiring layer. With such a configuration, the detection accuracy of one or the plurality of sensor units is improved.

In an exemplary aspect, the one or the plurality of energy irradiation units is arranged on the first main surface side of the wiring layer. With such a configuration, the irradiation efficiency of the energy irradiation unit is improved.

In an exemplary aspect, the functional portion has flexibility. According to such a configuration, the functional portion can be easily brought into contact with the measurement site or the irradiation site.

In an exemplary aspect, in the functional portion, the first insulating layer is provided with one or a plurality of openings, and at least one of the one or the plurality of sensor units and the one or the plurality of energy irradiation units is arranged in a region exposed from the one or the plurality of openings. With such a configuration, the performance of the oral appliance can be further improved.

In an exemplary aspect, in the one or the plurality of openings, two or more adjacent sensor units among the plurality of sensor units is arranged away from each other with a space. With such a configuration, the performance of the oral appliance is further improved.

In an exemplary aspect, the oral appliance can further include a correction sensor unit that is arranged at a position different from the one or the plurality of sensor units and acquires correction information for correcting information acquired by the one or the plurality of sensor units. With such a configuration, it is possible to acquire correction information for correcting information acquired by one or the plurality of sensor units.

In an exemplary aspect, the correction sensor unit is arranged in at least one of the wiring portion and the connection portion in the wiring layer. With such a configuration, it is possible to acquire information outside the oral cavity as the correction information.

In an exemplary aspect, the correction sensor unit is arranged side by side with the one or the plurality of sensor units along the first insulating layer in the wiring layer of the functional portion, and is configured to acquire information in the oral cavity with a detection sensitivity different from that of the one or the plurality of sensor units. With such a configuration, it is possible to acquire the correction information from the information in the oral cavity.

In an exemplary aspect, the electrical connection portion can be one or a plurality of electrodes exposed from at least one of the first insulating layer and the second insulating layer. With such a configuration, an electrical connection between the oral appliance and the oral body device is easily performed.

In an exemplary aspect, the electrical connection portion is an RFID tag. With such a configuration, the electrical connection between the oral appliance and the oral body device can be easily performed.

In an exemplary aspect, the oral appliance is configured in a bag shape in which the first main surface of the wiring layer is arranged to face outward and the second main surface of the wiring layer is arranged to face inward. With such a configuration, the oral appliance is more firmly fixed to the oral body device.

An exemplary embodiment of the present invention will be described below with reference to the accompanying drawings. Note that the following description is merely illustrative in nature and is not intended to limit the present disclosure, applications thereof, or uses thereof. Further, the drawings are schematic, and ratios of respective dimensions and the like do not necessarily match actual ones.

Embodiment 1

[Oral Device]

Figure 2:
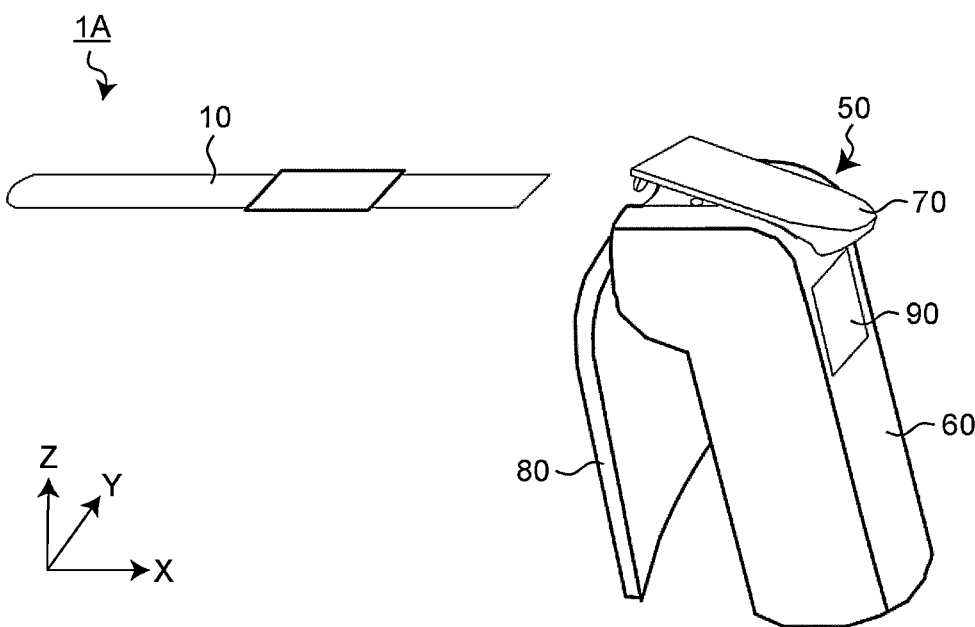
FIG. 2 is a schematic perspective view of an example of the oral device of Embodiment 1 according to an exemplary aspect.

FIG. 1 and FIG. 2 are schematic perspective views of an example of an oral device 1A of Embodiment 1 according to an exemplary aspect. FIG. 1 illustrates a state in which an oral appliance 10 is attached to an oral body device 50. FIG. 2 illustrates a state in which the oral appliance 10 is detached from the oral body device 50. X, Y, and Z directions in the figures indicate a length direction, a width direction, and a height direction of the oral device 1A, respectively.

As illustrated in FIG. 1 and FIG. 2, the oral device 1A includes the oral appliance 10 and the oral body device 50. The oral device 1A is a disposable-type device. In the oral device 1A, the oral appliance 10 to be used in the oral cavity is detachably attached to the oral body device 50. After the oral appliance 10 is attached to the oral body device 50 and used, the oral appliance 10 is detached from the oral body device 50.

The oral device 1A performs a function by bringing the oral appliance 10 into contact with a site in the oral cavity of a patient, for example. The function includes, for example, a sensing function and/or an energy irradiation function.

The sensing function acquires information related to biological information in the oral cavity. The biological information can be various physiological and anatomical pieces of information generated by a living body. The biological information is, for example, information on such as dryness (e.g., degree of wetness, amount of moisture), tongue pressure, occlusal force, chewing function, swallowing function, tongue-lip movement function, poor hygiene, saliva components, exhaled gas components, body temperature, and hardness. The information related to the biological information is, for example, information on such as electrostatic capacity, impedance (resistance), pressure, potential, color tone, temperature, hardness, and vibration. The oral device 1A brings the oral appliance 10 into contact with a measurement site in the oral cavity of the user, and acquires information related to biological information of the measurement site with which the oral appliance 10 has been brought into contact. The oral device 1A measures the state in the oral cavity by acquiring biological information with the oral body device 50 based on the information acquired by the oral appliance 10. The oral body device 50 measures, for example, an amount of moisture, an amount of salivation, an occlusal force, a tongue pressure, a color tone of the tongue, and/or an amount of various substances contained in saliva.

The energy irradiation function radiates energy into the oral cavity. In an exemplary aspect, the energy is, for example, energy such as light, heat, ultrasonic waves, or electromagnetic waves.

The oral device 1A can be used as, for example, a hygrometer, an occlusal force meter, a tongue pressure meter, a laser treatment device, a thermotherapy device, an ultrasonic echo, an ultrasonic treatment device, or an electromagnetic irradiation device.

In Embodiment 1, an example in which the oral device 1A is a hygrometer will be described.

Figure 3:
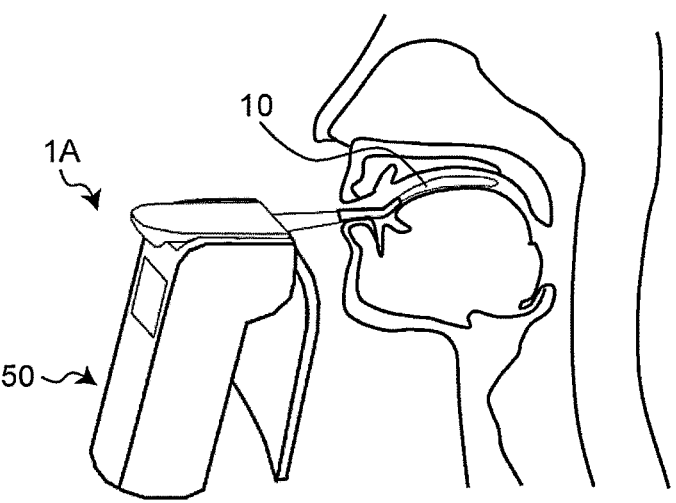
FIG. 3 is a schematic view illustrating an example of a state in which the oral device of Embodiment 1 is used according to an exemplary aspect.

FIG. 3 is a schematic view illustrating an example of a state in which the oral device 1A of Embodiment 1 according to an exemplary aspect is used. As illustrated in FIG. 3, the oral device 1A brings the oral appliance 10 into contact with a measurement site in the oral cavity of the user (e.g., a patient). The measurement site is, for example, the tongue portion, buccal mucosa, palate, or the like in the oral cavity. The oral appliance 10 comes into contact with the measurement site by deforming along the shape of the measurement site. The oral device 1A starts measurement in a state in which the oral appliance 10 is brought into contact with the measurement site in the oral cavity.

[Oral Appliance]

Figure 4:
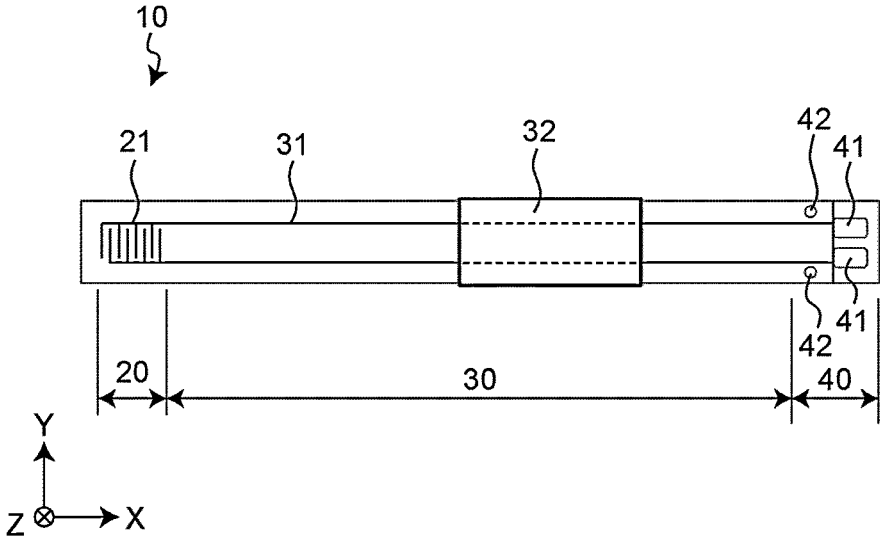
FIG. 4 is a schematic view illustrating an example of the oral appliance.
Figure 5:
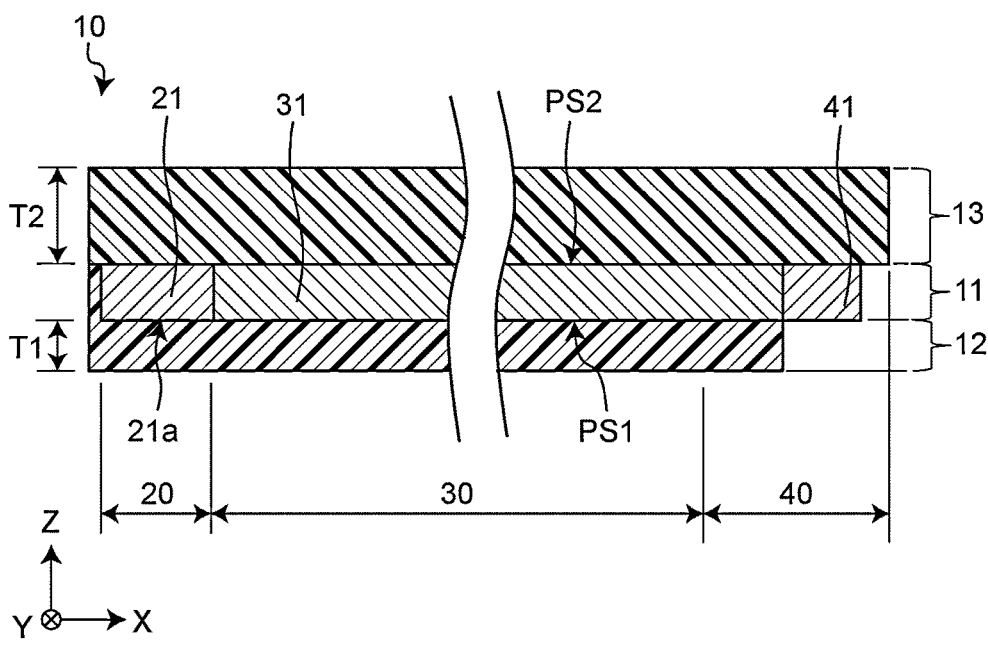
FIG. 5 is a schematic cross-sectional view illustrating the example of the oral appliance of FIG. 4 in an enlarged manner.
Figure 6:
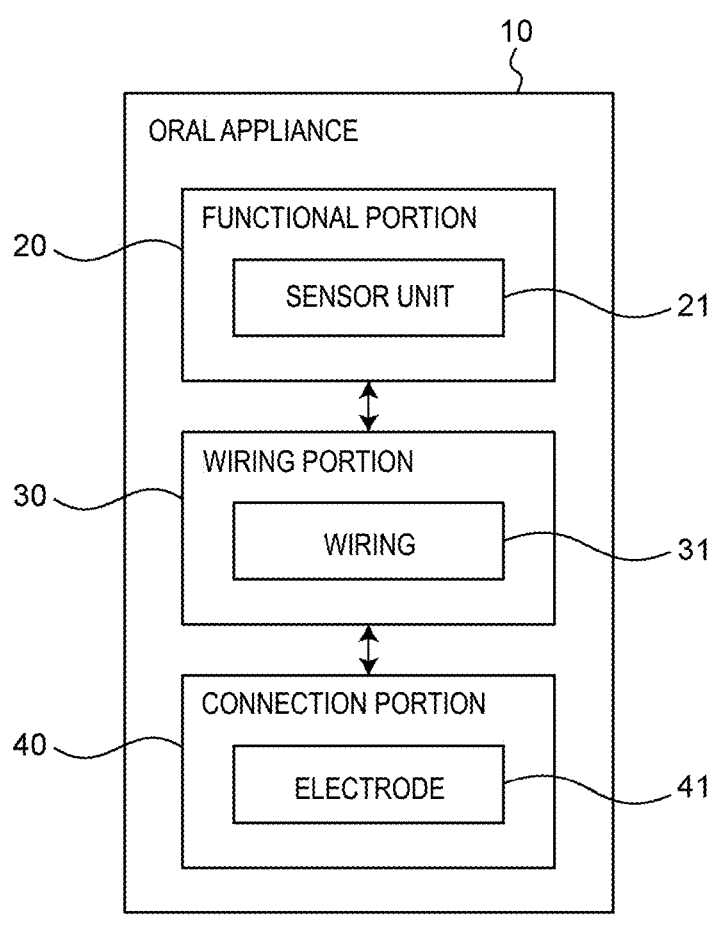
FIG. 6 is a block diagram illustrating a main configuration of an example of the oral appliance.

FIG. 4 is a schematic view illustrating an example of the oral appliance 10. FIG. 5 is a schematic cross-sectional view illustrating an example of the oral appliance 10 of FIG. 4 in an enlarged manner. FIG. 6 is a block diagram illustrating a configuration of an example of the oral appliance 10.

As illustrated in FIG. 4 to FIG. 6, the oral appliance 10 includes a functional portion 20, a wiring portion 30, and a connection portion 40.

In Embodiment 1, the oral appliance 10 is configured as a sensing probe that is attachable to and detachable from the oral body device 50. The oral appliance 10 is a sheet-shaped appliance having an electrical connection portion. The oral appliance 10 is formed in a rectangular sheet shape having a longitudinal direction. Note that the shape of the oral appliance 10 is not limited to a rectangular shape as long as the oral appliance 10 is formed in a sheet shape.

The electrical connection portion is electrically connected to the oral body device 50. In Embodiment 1, the electrical connection portion includes one or a plurality of electrodes 41.

The oral appliance 10 has flexibility and can be deformed. In the oral appliance 10, at least the functional portion 20 has flexibility.

<Functional Portion>

The functional portion 20 (or functional member) is a portion that exhibits a sensing function, and is provided on a front end side of the oral appliance 10. The functional portion 20 includes a sensor unit 21 that acquires information in the oral cavity. Moreover, the sensor unit 21 has a sensor surface 21*a* arranged on the measurement site side in the oral cavity of the user. The functional portion 20 acquires the information in the oral cavity by bringing the sensor surface 21*a* side of the sensor unit 21 into surface contact with the measurement site. In Embodiment 1, the sensor unit 21 includes an electrostatic capacity sensor and acquires electrostatic capacity.

The functional portion 20 is configured to be deformed along the shape of the measurement site when coming into contact with the measurement site in the oral cavity. Accordingly, the functional portion 20 can be easily brought into contact with the measurement site in the oral cavity. To be specific, the sensor surface 21*a* of the sensor unit 21 fits the shape of the measurement site due to the functional portion 20 deforming along the shape of the measurement site. Accordingly, since the entire sensor surface 21*a* can be arranged to be close to the measurement site, the information in the oral cavity can be easily acquired from the measurement site using the entire sensor surface 21*a*.

In Embodiment 1, an example in which the functional portion 20 has flexibility has been described, but the present invention is not limited thereto. In the oral appliance 10, at least the functional portion 20 may have flexibility. For example, the wiring portion 30 and/or the connection portion 40 may have flexibility.

<Wiring Portion>

The wiring portion 30 is arranged between the functional portion 20 and the connection portion 40. As shown, the wiring portion 30 includes a wiring 31 that electrically connects the functional portion 20 and the electrode 41 of the connection portion 40. The wiring 31 is formed of a conductive material, for example. Examples of the conductive material of the wiring 31 include Cu, Al, and Ag. For example, the wiring 31 is formed by a wiring conductor pattern.

In addition, the wiring portion 30 includes a protective layer 32 that covers the periphery of the wiring portion 30. The protective layer 32 is arranged at a portion where the teeth touch when the oral appliance 10 is arranged in the oral cavity. The protective layer 32 only needs to be arranged between the functional portion 20 and the connection portion 40. For example, the protective layer 32 is formed of a protective film having a thickness of equal to or more than 100 μm and equal to or less than 10 mm. The protective film may be formed of a material, such as resin or a foam, according to an exemplary aspect.

<Connection Portion>

The connection portion 40 is a portion to be attached to the oral body device 50, and is provided on a rear end side opposite to a front end of the oral appliance 10. The connection portion 40 includes one or the plurality of electrodes 41. In Embodiment 1, the connection portion 40 includes two electrodes 41. Note that the number of the electrodes 41 is not limited to two in alternative aspects.

The one or the plurality of electrodes 41 is formed of a material having conductivity. Examples of the material of the electrode 41 include Cu, Al, and SUS. In addition, the electrode 41 may be formed of a corrosion-resistant material such as Au, Ag, silver chloride, Ti, Pt, carbon, or a conductive polymer (for example, PEDOT or the like). The electrode 41 is formed of Cu and may be plated with Au, Ni, or the like.

In Embodiment 1, when the connection portion 40 is attached to the oral body device 50, the plurality of electrodes 41 is electrically connected by a physical contact with a plurality of connection terminals provided in the oral body device 50.

In addition, the connection portion 40 is provided with a mounting hole 42. The mounting hole 42 is a through-hole into which a protrusion 73*a* of an attachment/detachment operation unit 70 described later is inserted. In Embodiment 1, two mounting holes 42 are provided in the connection portion 40.

Note that the mounting hole 42 is not limited to a through-hole, and may be a notch or a recess in alternative aspects. The mounting hole 42 may have any size as long as the protrusion 73*a* of the attachment/detachment operation unit 70 can be inserted therein. In addition, the connection portion 40 only needs to be provided with one or a plurality of the mounting holes 42.

As illustrated in FIG. 5, the oral appliance 10 is composed of a wiring layer 11 and a plurality of insulating layers 12 and 13. In Embodiment 1, the wiring layer 11 and the plurality of insulating layers 12 and 13 are configured to be stacked. In addition, the plurality of insulating layers 12 and 13 includes the first insulating layer 12 and the second insulating layer 13.

<Wiring Layer>

The wiring layer 11 includes the sensor unit 21, the wiring 31, and the plurality of electrodes 41. The wiring layer 11 has a first main surface PS1 and a second main surface PS2 on the side opposite to the first main surface PS1. In the oral appliance 10, the first main surface PS1 side is a side that comes into contact with a measurement site in the oral cavity. In Embodiment 1, the sensor surface 21*a* of the sensor unit 21 is arranged on the first main surface PS1 side of the wiring layer 11.

On the first main surface PS1 side of the wiring layer 11, the plurality of electrodes 41 is exposed from the first insulating layer 12. It is noted that according to the exemplary aspect, the plurality of electrodes 41 only needs to be exposed from at least one of the first insulating layer 12 and the second insulating layer 13.

A thickness of the wiring layer 11 is preferably equal to or more than 1 μm and equal to or less than 50 μm, for example. More preferably, the thickness of the wiring layer 11 is equal to or more than 2 μm and equal to or less than 25 μm.

<Plurality of Insulating Layers>

The plurality of insulating layers 12 and 13 includes the first insulating layer 12 arranged on the first main surface PS1 of the wiring layer 11 and the second insulating layer 13 arranged on the second main surface PS2 of the wiring layer 11.

A thickness T1 of the first insulating layer 12 is smaller than a thickness T2 of the second insulating layer 13. The thickness T1 of the first insulating layer 12 is equal to or less than ½ times the thickness T2 of the second insulating layer 13. Preferably, a thickness T1 of the first insulating layer 12 in a functional portion 20 is equal to or less than ⅛ times a thickness T2 of the second insulating layer 13. The thickness T1 of the first insulating layer 12 is preferably equal to or more than 0.01 μm and equal to or less than 25 μm, for example. The thickness T2 of the second insulating layer 13 is preferably equal to or more than 10 μm and equal to or less than 200 μm, for example. It is also noted that the thickness T1 of the first insulating layer 12 refers to the thickness of the first insulating layer 12 located in the outer side portion of the first main surface PS1 of the wiring layer 11 in the Z direction. The thickness T2 of the second insulating layer 13 refers to the thickness of the second insulating layer 13 located in the outer side portion of the second main surface PS2 of the wiring layer 11 in the Z direction.

In Embodiment 1, an example in which the thickness T1 of the first insulating layer 12 is smaller than the thickness T2 of the second insulating layer 13 over the functional portion 20, the wiring portion 30, and the connection portion 40 will be described, but the present invention is not limited thereto. At least in the functional portion 20, the thickness T1 of the first insulating layer 12 only needs to be smaller than the thickness T2 of the second insulating layer 13.

In the functional portion 20, since the thickness T1 of the first insulating layer 12 is smaller than the thickness T2 of the second insulating layer 13, the detection accuracy of the sensor unit 21 on the first main surface PS1 side of the wiring layer 11 can be improved. That is, by making the thickness T1 of the first insulating layer 12 small, it is possible to reduce the influence of the first insulating layer 12 on the information acquisition of the sensor unit 21. Specifically, by making the thickness T1 of the first insulating layer 12 small, it is possible to reduce the distance between the sensor surface 21a of the sensor unit 21 and the measurement site. This makes it easy to acquire information from the sensor surface 21a, whereby the detection accuracy of the sensor unit 21 can be improved. In this way, by making the thickness T1 of the first insulating layer 12 smaller than the thickness T2 of the second insulating layer 13, it is possible to improve the detection accuracy of the sensor unit 21 while protecting the functional portion 20. Further, by making the thickness T1 of the first insulating layer 12 smaller than the thickness T2 of the second insulating layer 13, it becomes easier to acquire information from the first main surface PS1 side than from the second main surface side. Alternatively, the detection direction of the oral appliance 10 can be limited to the first main surface PS1 side by designing the thickness T2 of the second insulating layer 13 to be thin enough that the thickness cannot be detected by the sensor unit 21.

The plurality of insulating layers 12 and 13 is formed of an insulating material. Examples of the insulating material include polyethylene (PE), polypropylene (PP), polyethylene terephthalate (PET), nylon, polyvinyl chloride, polyimide, and the like.

For example, the wiring layer 11 and the plurality of insulating layers 12 and 13 may be formed of a flexible printed circuit board.

It is also noted that the oral appliance 10 described above is an example, and the configuration of the oral appliance 10 is not limited thereto. The oral appliance 10 may be any sheet-shaped appliance having an electrical connection portion. Alternatively, the oral appliance 10 may include a shield layer in addition to the wiring layer 11 and the plurality of insulating layers 12 and 13. Moreover, the plurality of insulating layers may include two or more insulating layers.

[Oral Body Device]

Figure 7:
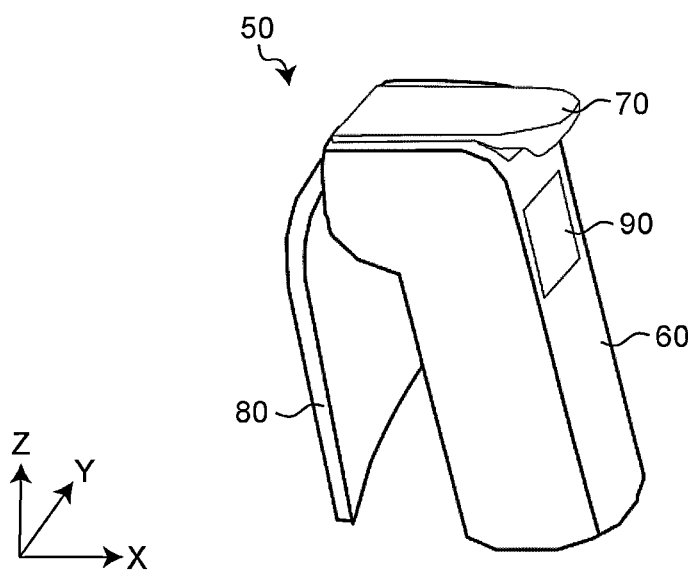
FIG. 7 is a schematic perspective view of an example of an oral body device.
Figure 8:
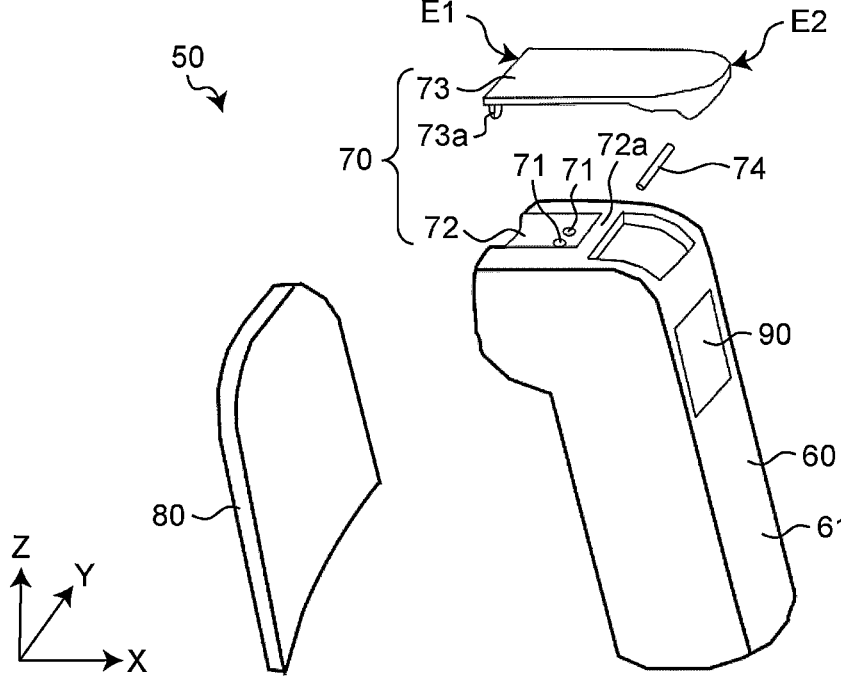
FIG. 8 is a schematic exploded view of the example of the oral body device of FIG. 7.
Figure 9:
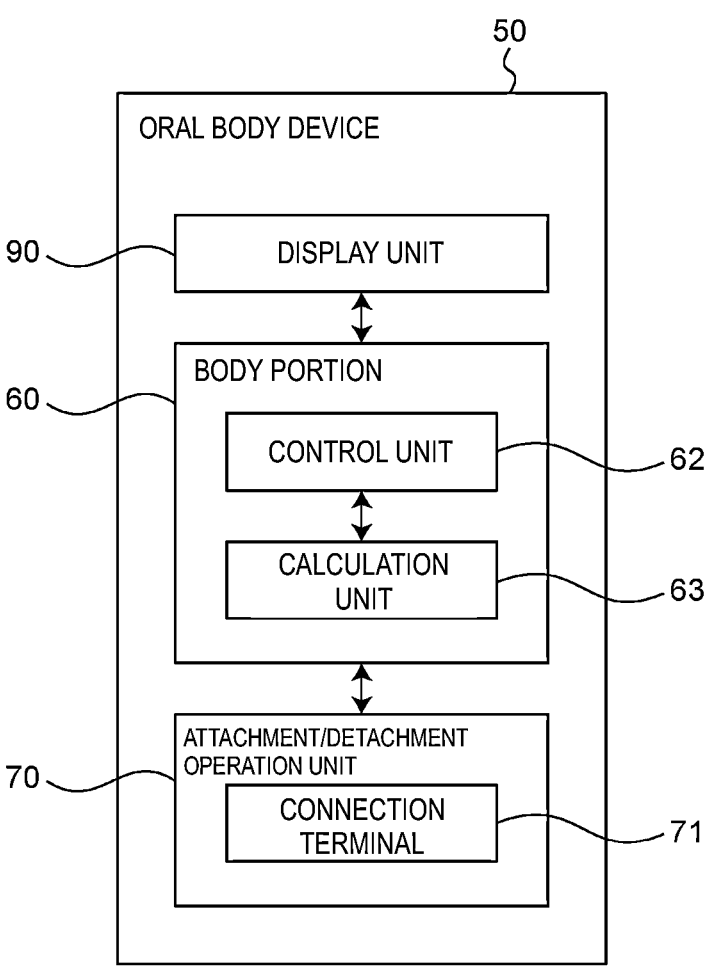
FIG. 9 is a block diagram illustrating a main configuration of an example of the oral body device.

FIG. 7 is a schematic perspective view of an example of the oral body device 50. FIG. 8 is a schematic exploded view of the example of the oral body device 50 of FIG. 7. FIG. 9 is a block diagram illustrating a configuration of an example of the oral body device 50. Note that, hereinafter, the oral body device 50 may be referred to as the body device 50 for purposes of this disclosure.

As illustrated in FIG. 7 to FIG. 9, the body device 50 includes a body portion 60, the attachment/detachment operation unit 70, a guard 80, and a display unit 90. Note that in Embodiment 1, an example in which the body device 50 includes the guard 80 and the display unit 90 will be described, but the present invention is not limited thereto. The guard 80 and the display unit 90 are not essential components. For example, the display unit 90 may be provided in a device different from the body device 50.

In the body device 50, the oral appliance 10 can be detachably attached to the attachment/detachment operation unit 70. Further, the body device 50 is configured to calculate the amount of a measurement target based on the information related to the biological information acquired by the oral appliance 10. Specifically, the body device 50 calculates the amount of moisture (e.g., a degree of wetness) based on the electrostatic capacity acquired by the oral appliance 10.

<Body Portion>

The body portion 60 is a body portion of the body device 50. The body portion 60 is formed of a rod-shaped member having a longitudinal direction. The body portion 60 includes a grip portion 61 to be gripped by a user. The grip portion 61 is formed by the external shape of the body portion 60.

The attachment/detachment operation unit 70 is arranged on one end side of the body portion 60. The guard 80 and the display unit 90 are arranged in the body portion 60.

The body portion 60 includes a control unit 62 and a calculation unit 63.

The control unit 62 integrally controls the components forming the oral device 1A. The control unit 62 includes, for example, a memory storing a program and a processing circuit corresponding to a processor such as a central processing unit (CPU). For example, in the control unit 62, the processor executes a program stored in the memory to perform the algorithms and functions described herein.

The control unit 62 controls the calculation unit 63 and the display unit 90.

The calculation unit 63 is configured to calculate the amount of a measurement target based on the information acquired by the oral appliance 10. In Embodiment 1, the calculation unit 63 calculates the amount of moisture based on the electrostatic capacity acquired by the oral appliance 10.

The calculation unit 63 can be realized by a semiconductor element or the like. The function of the calculation unit 63 may be configured only by hardware or may be realized by a combination of hardware and software.

In Embodiment 1, the calculation unit 63 includes a moisture content calculation circuit. The moisture content calculation circuit calculates the amount of moisture from the electrostatic capacity acquired by the oral appliance 10 based on a relational expression between the electrostatic capacity and the amount of moisture.

Information on the amount of moisture calculated by the calculation unit 63 is transmitted to the display unit 90.

<Attachment/Detachment Operation Unit>

The attachment/detachment operation unit 70 is configured to detachably attach the oral appliance 10 to the body portion 60 by operating application and release of a force with respect to the oral appliance 10. In Embodiment 1, the attachment/detachment operation unit 70 is configured to detachably attach the oral appliance 10 in a direction intersecting a direction in which the body portion 60 extends. That is, an attachment/detachment direction of the oral appliance 10 is a direction intersecting the direction in which the body portion 60 extends.

The attachment/detachment operation unit 70 has an electrical connection conductor. The electrical connection conductor is a conductor that is electrically connected to the oral appliance 10. Specifically, the electrical connection conductor is electrically connected to an electrical connection portion of the oral appliance 10. In Embodiment 1, the electrical connection conductor is one or a plurality of connection terminals 71. The one or the plurality of connection terminals 71 is formed of a material having conductivity. The one or the plurality of connection terminals 71 is electrically connected by a physical contact with the one or the plurality of electrodes 41 provided at the connection portion 40 of the oral appliance 10.

The attachment/detachment operation unit 70 fixedly attaches the oral appliance 10 in a state in which the electrode 41 and the connection terminal 71 are electrically connected by applying a force to the connection portion 40 of the oral appliance 10. In addition, the attachment/detachment operation unit 70 releases the fixation and detaches the oral appliance 10 by releasing the force applied to the connection portion 40 of the oral appliance 10. Further, when the oral appliance 10 is detached, the electrical connection between the electrode 41 and the connection terminal 71 may be released.

The attachment/detachment operation unit 70 includes an arrangement surface 72 on which the oral appliance 10 is arranged, and a pressing member 73 that applies a force in a direction intersecting the arrangement surface 72. In Embodiment 1, the pressing member 73 is arranged above the arrangement surface 72.

The arrangement surface 72 is provided on an end surface on one end side of the body portion 60. The arrangement surface 72 is a surface on which the oral appliance 10 can slide. The arrangement surface 72 may be formed by denting the end surface on the one end side of the body portion 60 in a concave shape, or may be formed as a flat surface.

As further shown, the one or the plurality of connection terminals 71 is arranged on the arrangement surface 72. The one or the plurality of connection terminals 71 is arranged at positions corresponding to the one or the plurality of electrodes 41 when the oral appliance 10 is arranged and fixed on the arrangement surface 72. In Embodiment 1, two connection terminals 71 are arranged on the arrangement surface 72. Note that the number of the connection terminals 71 is not limited to two.

The arrangement surface 72 is provided with a positioning member 72a extending toward the pressing member 73. The positioning member 72a determines the position in the X direction on the arrangement surface 72. For example, the positioning member 72a may be formed by a step formed on the arrangement surface 72, or may be formed to protrude in a convex shape from the arrangement surface 72 toward the pressing member 73. For example, when the oral appliance 10 is slid in the X direction and arranged on the arrangement surface 72, the oral appliance 10 is slid until an end portion of the connection portion 40 of the oral appliance 10 comes into contact with the positioning member 72a. As described above, when the oral appliance 10 is attached to the attachment/detachment operation unit 70, the oral appliance 10 is slid until coming into contact with the positioning member 72a, whereby the position of the oral appliance 10 in the X direction can be easily determined. This configuration facilitates attachment at a position where the electrode 41 of the oral appliance 10 and the connection terminal 71 arranged on the arrangement surface 72 are in physical contact with each other, and electrical connection can be easily performed.

The pressing member 73 is a member configured for operating application and release of a force to the oral appliance 10. The pressing member 73 is configured to apply the force in a direction intersecting the arrangement surface 72. Thus, the pressing member 73 can fix the oral appliance 10 to the arrangement surface 72 in a state in which the electrode 41 and the connection terminal 71 are electrically connected.

Moreover, the pressing member 73 is formed of a plate-shaped member having one end E1 and another end E2. The one end E1 is provided on the arrangement surface 72 side. The other end E2 is provided on a side opposite to the one end E1. A rotation shaft 74 is arranged between the one end E1 and the other end E2 of the pressing member 73. The pressing member 73 is configured to be rotatable around the rotation shaft 74. In addition, the one end E1 of the pressing member 73 is biased in a direction approaching the arrangement surface 72 by, for example, an elastic body. Examples of the elastic body include a spring, rubber, and the like.

The pressing member 73 has the protrusion 73a protruding toward the arrangement surface 72 between the one end E1 and the rotation shaft 74. The protrusion 73a is inserted into the mounting hole 42 provided in the connection portion 40 of the oral appliance 10. In Embodiment 1, the pressing member 73 has two protrusions 73a provided at the one end E1 of the pressing member 73. Note that the pressing member 73 only needs to have one or the plurality of protrusions 73a.

The attachment/detachment operation unit 70 operates application and release of the force to the oral appliance 10 by operating a rotational motion of the pressing member 73. To be specific, in a state in which the pressing member 73 is not operated, the one end E1 of the pressing member 73 moves in a direction approaching the arrangement surface 72 by a biasing force of the elastic body, thereby pressing against the oral appliance 10 arranged on the arrangement surface 72. Accordingly, the oral appliance 10 is fixed so as to be sandwiched between the arrangement surface 72 and the pressing member 73, and the oral appliance 10 can be attached to the attachment/detachment operation unit 70. In addition, by inserting the protrusion 73a of the pressing member 73 into the mounting hole 42 of the connection portion 40, the oral appliance 10 can be fixed so as not to be detached from the attachment/detachment operation unit 70.

When the oral appliance 10 is detached from the attachment/detachment operation unit 70, the one end E1 of the pressing member 73 moves in a direction away from the arrangement surface 72 by pressing down the other end E2 of the pressing member 73. Accordingly, a pressing force against the oral appliance 10 by the pressing member 73 is released, and the oral appliance 10 can be detached from the attachment/detachment operation unit 70. In this way, since the oral appliance 10 can be detached by the operation of the attachment/detachment operation unit 70, the oral appliance 10 can be easily detached without touching the used oral appliance 10.

Note that in Embodiment 1, an example in which the pressing member 73 is biased by an elastic body has been described, but the exemplary aspects of present invention are not limited thereto. In the pressing member 73, the force may be applied to the pressing member 73 in a direction intersecting the arrangement surface 72 by a mechanism other than the elastic body, for example, a lock mechanism, a slide mechanism, and/or an electromagnetic force. In addition, a suction portion may be provided to apply a force to the oral appliance 10 by a suction force.

<Guard>

The guard 80 is arranged on the body portion 60 and protects the grip portion 61. When the user uses the oral device 1A, the guard 80 suppresses saliva from adhering to the hand of the user holding the grip portion 61.

In Embodiment 1, the guard 80 is arranged on the side of the body portion 60 to which the oral appliance 10 is attached. The side where the oral appliance 10 is attached refers to the side where the oral appliance 10 is attached and detached. In addition, the guard 80 is formed of a plate-shaped member.

<Display Unit>

The display unit 90 is arranged in the body portion 60 and displays information on the oral device 1A. The information on the oral device 1A includes, for example, information on a measurement subject.

In Embodiment 1, the information on the measurement subject is information on the amount of moisture. For example, the calculation unit 63 calculates the amount of moisture based on the electrostatic capacity acquired by the oral appliance 10. The calculation unit 63 transmits information on the amount of moisture to the display unit 90.

The display unit 90 is, for example, a display such as an electronic display.

Note that the body device 50 may include an input unit for inputting input information from the user. For example, the input unit may have one or a plurality of buttons for receiving an input from the user. The one or the plurality of buttons may include, for example, a power button for switching power ON/OFF, a measurement start button for starting measurement, and the like.

[Example of Oral Appliance Attached to Attachment/Detachment Operation Unit]

Figure 10:
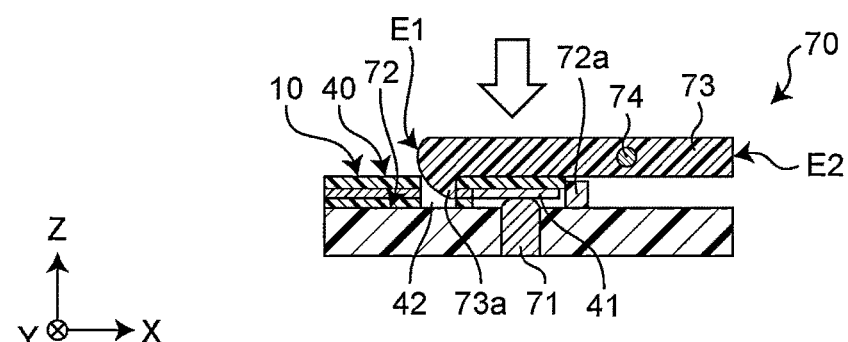
FIG. 10 is a schematic partially enlarged cross-sectional view illustrating an example of the oral appliance attached to an attachment/detachment operation unit in an enlarged manner.

An example of the oral appliance 10 attached to the attachment/detachment operation unit 70 will be described with reference to FIG. 10, and FIG. 10 is a schematic partially enlarged cross-sectional view illustrating an example of the oral appliance 10 attached to the attachment/detachment operation unit 70 in an enlarged manner.

As illustrated in FIG. 10, the oral appliance 10 is arranged on the arrangement surface 72 of the attachment/detachment operation unit 70. To be specific, the connection portion 40 of the oral appliance 10 is positioned by being brought into contact with the positioning member 72a and is arranged on the arrangement surface 72. In addition, the connection portion 40 of the oral appliance 10 is positioned at a position where the electrode 41 and the connection terminal 71 are in physical contact with each other by the positioning member 72a. Thus, the electrode 41 of the oral appliance 10 and the connection terminal 71 of the body device 50 are electrically connected to each other. When the electrode 41 of the oral appliance 10 and the connection terminal 71 of the body device 50 are electrically connected to each other, the oral appliance 10 can be used by the body device 50.

The pressing member 73 presses the connection portion 40 of the oral appliance 10 toward the arrangement surface 72 by the biasing force of the elastic body. Thus, the connection portion 40 of the oral appliance 10 is sandwiched and fixed between the arrangement surface 72 and the pressing member 73.

Further, the protrusion 73a provided at the one end E1 of the pressing member 73 is inserted into the mounting hole 42 of the connection portion 40 of the oral appliance 10. As such, it is possible to suppress the oral appliance 10 from falling off from the attachment/detachment operation unit 70.

In this manner, the oral appliance 10 is fixedly attached to the body device 50 in a state in which the electrode 41 and the connection terminal 71 are electrically connected to each other by being applied with the pressing force by the pressing member 73. In addition, by releasing the pressing force of the pressing member 73, the fixation is released and the oral appliance 10 can be easily detached from the body device 50.

[Effects]

According to the oral appliance 10 according to Embodiment 1, the following effects are achieved.

As described above, the oral appliance 10 is a sheet-shaped oral appliance that is detachably attached to the oral body device 50. The oral appliance 10 includes the functional portion 20, the connection portion 40, and the wiring portion 30. The functional portion 20 includes the sensor unit 21 that acquires information in the oral cavity. The connection portion 40 has an electrical connection portion. The wiring portion 30 includes the wiring 31 that connects the sensor unit 21 and the electrical connection portion. The functional portion 20, the connection portion 40, and the wiring portion 30 are composed of the wiring layer 11 and the plurality of insulating layers 12 and 13. The wiring layer 11 has the first main surface PS1 and the second main surface PS2 on the side opposite to the first main surface PS1. The plurality of insulating layers 12 and 13 includes the first insulating layer 12 arranged on the first main surface PS1 of the wiring layer 11 and the second insulating layer 13 arranged on the second main surface PS2 of the wiring layer 11. Moreover, the thickness T1 of the first insulating layer 12 is smaller than the thickness T2 of the second insulating layer 13 in the functional portion 20.

With this configuration, the performance of the oral appliance 10 that is detachably attached to the oral body device 50 is improved. Specifically, by making the thickness T1 of the first insulating layer 12 smaller than the thickness T2 of the second insulating layer 13, the influence of the first insulating layer 12 on the sensor unit 21 on the first main surface PS1 side of the wiring layer 11 can be reduced. Thus, the distance between the sensor unit 21 and the measurement site can be reduced while protecting the functional portion 20 and improving the sensitivity of the sensor unit 21. As a result, the detection accuracy of the sensor unit 21 is also improved.

The wiring layer 11 and the plurality of insulating layers 12 and 13 are configured to be stacked. With such a configuration, the thickness of the oral appliance 10 can be reduced to facilitate insertion into the oral cavity. Since the oral appliance 10 can be made thin, it can be used by people who cannot open their mouth wide, such as, for example, patients with arthrosis of temporomandibular joint.

The wiring portion 30 includes the protective layer 32 arranged on the outer periphery of the wiring portion 30. With such a configuration, when the oral appliance 10 is inserted into the oral cavity to be used, the protective layer 32 is arranged at a position where the teeth of the user touch. Accordingly, it is possible to protect the wiring portion 30 by the protective layer 32, and it is possible to suppress a failure such as disconnection of the wiring 31 due to contact of the teeth of the user with the wiring portion 30.

The sensor unit 21 has the sensor surface 21*a* that acquires information on the measurement site in the oral cavity. The sensor surface 21*a* is arranged on the first main surface PS1 side of the wiring layer 11. With such a configuration, the detection accuracy of the sensor unit 21 is also improved.

In the oral appliance 10, at least the functional portion 20 has flexibility. With such a configuration, the functional portion 20 can be arranged to be deformed along the shape of the measurement site in the oral cavity. Accordingly, the contact area between the functional portion 20 and the measurement site can be increased. As a result, it is possible to acquire information in the oral cavity by fitting the sensor unit 21 to the measurement site, and thus it is possible to improve the detection accuracy.

Moreover, the electrical connection portion is the one or the plurality of electrodes 41 exposed from at least one of the first insulating layer 12 and the second insulating layer 13. With such a configuration, electrical connection can easily be achieved between the oral appliance 10 and the body device 50 by physical contact.

Note that in Embodiment 1, an example in which the oral device 1A is an oral moisture meter that measures the amount of moisture in the oral cavity has been described, but the exemplary aspects of the present invention are not limited thereto. The oral device 1A may be any device that acquires information in the oral cavity and/or any device that radiates energy into the oral cavity.

Although an example in which the oral appliance 10 has flexibility has been described in Embodiment 1, the exemplary aspects of the present invention are not limited thereto. It is noted that in the oral appliance 10, the flexibility is not an essential component. That is, the oral appliance 10 need not have flexibility.

Although an example in which the oral appliance 10 includes one sensor unit 21 has been described in Embodiment 1, the exemplary aspects of the present invention are not limited thereto. The oral appliance 10 may include at least one of the one or the plurality of the sensor units 21 and one or a plurality of energy irradiation units.

Although an example in which the sensor unit 21 of the oral appliance 10 includes an electrostatic capacity sensor has been described in Embodiment 1, the exemplary aspects of the present invention are not limited thereto. For example, the sensor unit 21 only needs to include a sensor that can acquire information related to biological information. For example, the sensor unit 21 only needs to include at least one of an impedance measurement sensor, a resistance sensor, a weight sensor, a humidity sensor, a pressure sensor, a color sensor, a temperature sensor, a hardness sensor, a vibration sensor, a biosensor, and the like.

In Embodiment 1, an example in which the calculation unit 63 calculates the amount of moisture based on the amount of change in frequency from the electrostatic capacity has been described, but the exemplary aspects of the present invention are not limited thereto. The calculation unit 63 only needs to be able to calculate information in the oral cavity based on the information acquired by the oral appliance 10.

In Embodiment 1, an example in which the oral appliance 10 is attached and detached by applying and releasing the pressing force with respect to the oral appliance 10 by the pressing member 73 has been described, but the exemplary aspects of the present invention are not limited thereto. For example, the oral appliance 10 may be attached and detached by the pressing force and/or the electromagnetic force by the pressing member 73. For example, the electrode 41 of the oral appliance 10 may be formed of a metal that reacts to magnets. Examples of the metal that reacts to magnets include iron, cobalt, nickel, and the like. Further, the body device 50 may be provided with a magnet. The electrode 41 of the oral appliance 10 may be attracted to the arrangement surface 72 by the magnetic force of the magnet provided in the body device 50.

In Embodiment 1, an example in which the electrical connection portion of the oral appliance 10 is the electrode 41 and the electrical connection conductor of the body device 50 is the connection terminal 71 has been described, but the exemplary aspects of the present invention are not limited thereto. Further, a "state in which the electrical connection portion and the electrical connection conductor are electrically connected" is not limited to a state in which the electrical connection portion and the electrical connection conductor are physically in contact with each other. For example, the "state in which the electrical connection portion and the electrical connection conductor are electrically connected" may include a state in which the electrical connection portion and the electrical connection conductor are electrically connected in a non-contact manner. For example, the electrical connection may be realized by wirelessly connecting the electrical connection portion and the electrical connection conductor using a wireless communication device such as an RFID tag.

In Embodiment 1, an example in which the functional portion 20 includes the sensor unit 21 has been described, but the exemplary aspects of the present invention are not limited thereto. The functional portion 20 only needs to include at least one of the sensor unit 21 that acquires information in the oral cavity and an energy irradiation unit 22 that radiates energy into the oral cavity.

In Embodiment 1, an example in which the functional portion 20 has flexibility has been described, but the exemplary aspects of the present invention are not limited thereto. In the oral appliance 10, at least the functional portion 20 may have flexibility. For example, the entire oral appliance 10 may have flexibility.

In Embodiment 1, an example in which the wiring portion 30 includes the protective layer 32 has been described, but the exemplary aspects of the present invention are not limited thereto. For example, the wiring portion 30 does not have to include the protective layer 32.

(Modification 1)

Figure 11A:
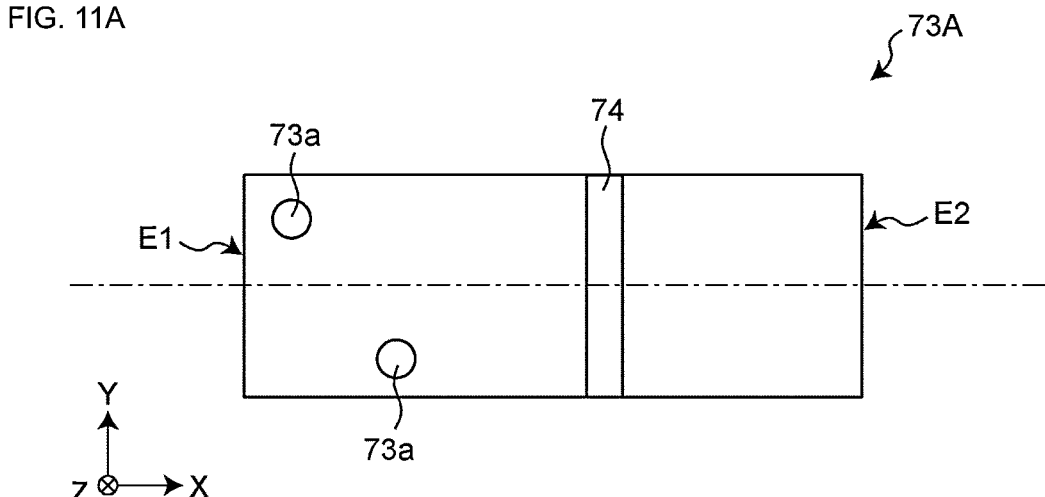
FIG. 11A is a schematic view illustrating an attachment/detachment operation unit of Modification 1 according to an exemplary aspect.
Figure 11B:
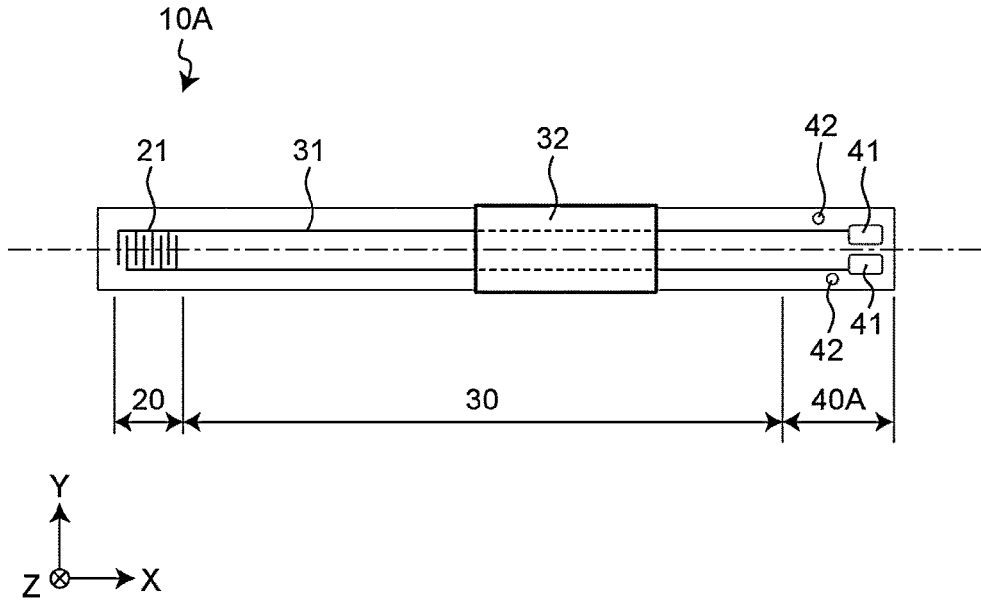
FIG. 11B is a schematic view illustrating an oral appliance of Modification 1 according to an exemplary aspect.

FIG. 11A is a schematic view illustrating a pressing member 73A of Modification 1 of the exemplary aspect described above. FIG. 11B is a schematic view illustrating an oral appliance 10A of Modification 1. As illustrated in FIG. 11A, when the pressing member 73A is viewed from the Z direction, the two protrusions 73*a* are arranged to be bilaterally asymmetric with respect to a center line extending in the X direction. In addition, as illustrated in FIG. 11B, when the oral appliance 10A is viewed from the Z direction, the two mounting holes 42 in a connection portion 40A are arranged to be bilaterally asymmetric with respect to a center line extending in the X direction. With such a configuration, the attachment direction of the oral appliance 10A can be defined. Thus, the oral appliance 10A can be attached to an attachment/detachment operation unit 70A without making a mistake in selecting the front surface or the back surface thereof (Modification 2)

Figure 12:
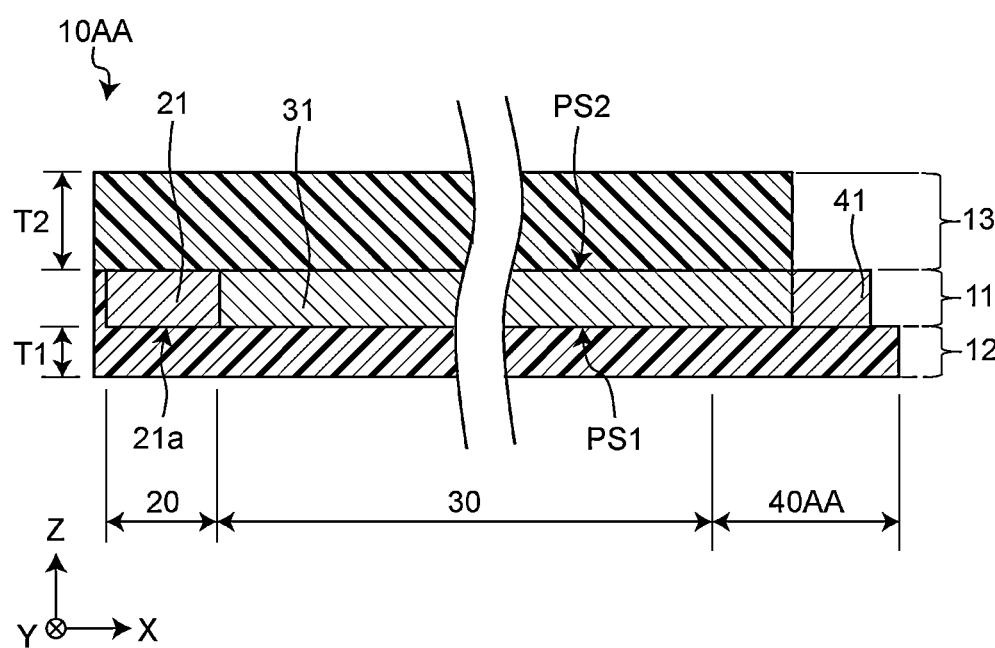
FIG. 12 is a schematic cross-sectional view illustrating an oral appliance of Modification 2 in an enlarged manner according to an exemplary aspect.

FIG. 12 is a schematic cross-sectional view illustrating an oral appliance 10AA of Modification 2 of the exemplary aspect described above in an enlarged manner. As illustrated in FIG. 12, in a connection portion 40AA of the oral appliance 10AA, the electrode 41 is exposed from the second insulating layer 13. Meanwhile, the electrode 41 is not exposed from the first insulating layer 12. In this case, in the attachment/detachment operation unit 70, the connection terminal 71 may be arranged on the pressing member 73. With such a configuration, the oral appliance 10AA and the body device 50 can be electrically connected to each other.

Embodiment 2

An oral appliance according to Embodiment 2 of an exemplary aspect will be described. Note that in Embodiment 2, differences from Embodiment 1 will be mainly described. In Embodiment 2, configurations identical or equivalent to those in Embodiment 1 are denoted by the same reference numerals to be described. Further, in Embodiment 2, the description overlapping with Embodiment 1 will be omitted.

Figure 13:
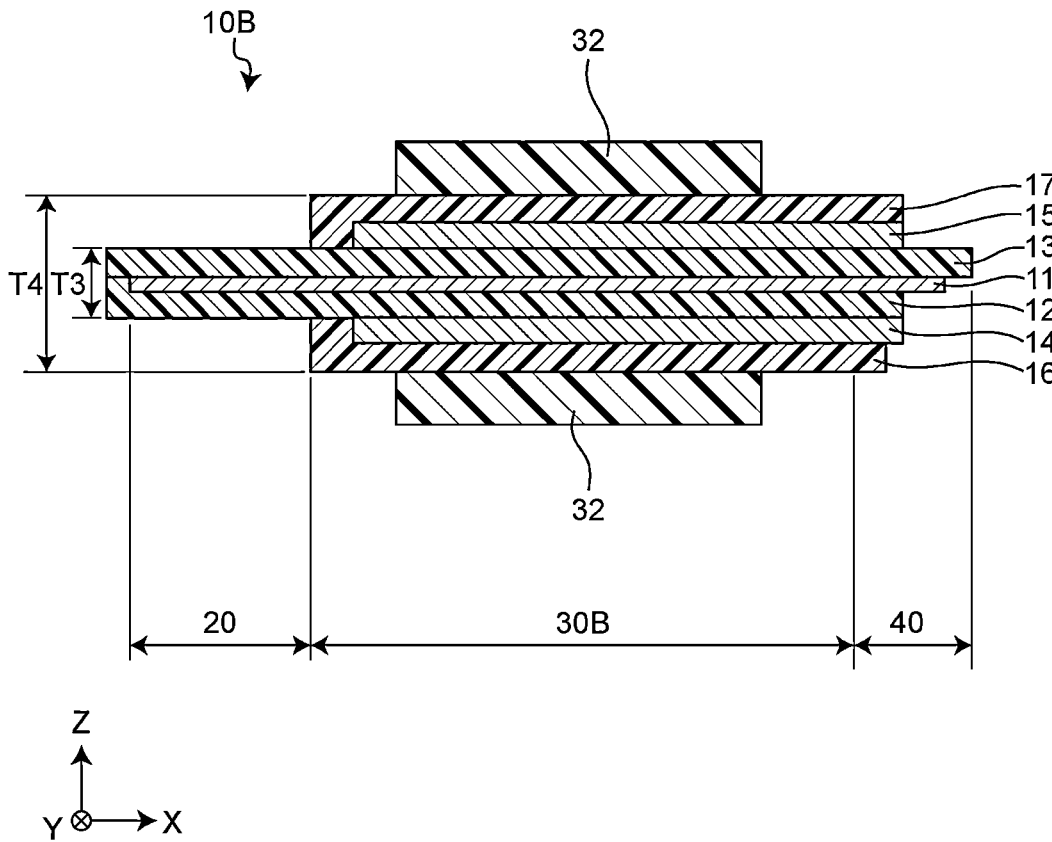
FIG. 13 is a schematic cross-sectional view illustrating an example of an oral appliance of Embodiment 2 according to an exemplary aspect in an enlarged manner.

An example of the oral appliance of Embodiment 2 will be described with reference to FIG. 13. FIG. 13 is a schematic cross-sectional view illustrating an example of an oral appliance 10B of Embodiment 2 according to the present invention in an enlarged manner.

Embodiment 2 is different from Embodiment 1 in that a thickness T4 of a wiring portion 30B is larger than a thickness T3 of the functional portion 20 and that a plurality of shield layers 14 and 15 is provided.

As illustrated in FIG. 13, in the oral appliance 10B, the thickness T4 of the wiring portion 30B is larger than the thickness T3 of the functional portion 20. For example, the thickness T4 of the wiring portion 30B is equal to or more than 2 times and equal to or less than 1000 times the thickness T3 of the functional portion 20.

By making the thickness T4 of the wiring portion 30B larger than the thickness T3 of the functional portion 20, it is possible to improve the strength of the wiring portion 30B.

As further shown, the wiring portion 30B includes the plurality of shield layers 14 and 15 arranged on the plurality of insulating layers 12 and 13 and a plurality of insulating layers 16 and 17. The wiring portion 30B is configured such that the wiring layer 11, the plurality of insulating layers 12, 13, 16, and 17, and the plurality of shield layers 14 and 15 are stacked.

In Embodiment 2, the plurality of insulating layers 12, 13, 16, and 17 includes the third insulating layer 16 and the fourth insulating layer 17 in addition to the first insulating layer 12 and the second insulating layer 13. The first insulating layer 12 and the third insulating layer 16 are arranged on the first main surface PS1 side of the wiring layer 11. The second insulating layer 13 and the fourth insulating layer 17 are arranged on the second main surface PS2 side of the wiring layer 11.

In Embodiment 2, the plurality of shield layers 14 and 15 includes two shield layers. Specifically, the plurality of shield layers 14 and 15 includes the first shield layer 14 and the second shield layer 15.

The first shield layer 14 is arranged on the first main surface PS1 side of the wiring layer 11, and is arranged between the first insulating layer 12 and the third insulating layer 16. In particular, the wiring layer 11, the first insulating layer 12, the first shield layer 14, and the third insulating layer 16 are stacked in this order on the first main surface PS1 side of the wiring layer 11 in the wiring portion 30B.

The second shield layer 15 is arranged on the second main surface PS2 side of the wiring layer 11, and is arranged between the second insulating layer 13 and the fourth insulating layer 17. In particular, the wiring layer 11, the second insulating layer 13, the second shield layer 15, and the fourth insulating layer 17 are stacked in this order on the second main surface PS2 side of the wiring layer 11 in the wiring portion 30B.

The plurality of shield layers 14 and 15 forms GND. The plurality of shield layers 14 and 15 is formed of, for example, a metal such as Cu, Ag, Au, or Al, or a carbon material. The thickness of each of the first shield layer 14 and the second shield layer 15 is equal to or more than 1 μm and equal to or less than 100 μm.

For example, the wiring layer 11 and the plurality of insulating layers 12, 13, 16, and 17 and the plurality of shield layers 14 and 15 may be formed of a multilayer flexible printed circuit board. Alternatively, the plurality of shield layers 14 and 15 may be formed by attaching a conductive nonwoven fabric or a metal foil to the plurality of insulating layers 12, 13, 16, and 17. Alternatively, the plurality of insulating layers 12, 13, 16, and 17 and the plurality of shield layers 14 and 15 may be formed using a film with metal film in which an insulating layer and a shield layer are integrally formed, and may be attached to the wiring layer 11.

[Effects]

According to the oral appliance 10B according to Embodiment 2, the following effects can be achieved.

In the oral appliance 10B, the thickness T4 of the wiring portion 30B is larger than the thickness T3 of the functional portion 20. With such a configuration, the mechanical strength of the wiring portion 30B is improved. For example, when the oral appliance 10B is inserted into the oral cavity, the wiring portion 30B may be bitten by the user's teeth. By increasing the thickness T4 of the wiring portion 30B to improve the mechanical strength, deformation of the wiring portion 30B can be suppressed. Accordingly, it is possible to suppress the occurrence of a failure such as disconnection of the wiring 31 when an external force is applied to the wiring portion 30B.

In addition, the wiring portion 30B includes the plurality of shield layers 14 and 15 arranged on the plurality of insulating layers 12 and 13. With such a configuration, noise generated from the wiring portion 30B can be suppressed. In addition, by forming the plurality of shield layers 14 and 15 with a material having high rigidity such as metal or carbon, it is possible to further improve the mechanical strength of the wiring portion 30B.

Note that In Embodiment 2, an example in which the wiring portion 30B includes the plurality of shield layers 14 and 15 has been described, but the exemplary aspects of the present invention are not limited thereto. For example, the wiring portion 30B need not include the plurality of shield layers 14 and 15.

In Embodiment 2, an example in which the wiring portion 30B includes two shield layers 14 and 15 has been described, but the exemplary aspects of the present invention are not limited thereto. The wiring portion 30B may include one or a plurality of shield layers.

In Embodiment 2, an example in which the first shield layer 14 is arranged between the first insulating layer 12 and the third insulating layer 16, and the second shield layer 15 is arranged between the second insulating layer 13 and the fourth insulating layer 17 has been described, but the present invention is not limited thereto. For example, the first shield layer 14 may be arranged between the wiring layer 11 and the first insulating layer 12. The second shield layer 15 may be arranged between the wiring layer 11 and the second insulating layer 13. The first shield layer 14 and/or the second shield layer 15 may be formed as a GND pattern adjacent to the wiring 31 in the wiring layer 11.

Embodiment 3

An oral device according to Embodiment 3 of an exemplary aspect will be described. Note that in Embodiment 3, differences from Embodiment 1 will be mainly described. In Embodiment 3, configurations identical or equivalent to those in Embodiment 1 are denoted by the same reference numerals to be described. Further, in Embodiment 3, the description overlapping with Embodiment 1 will be omitted.

Figure 14A:
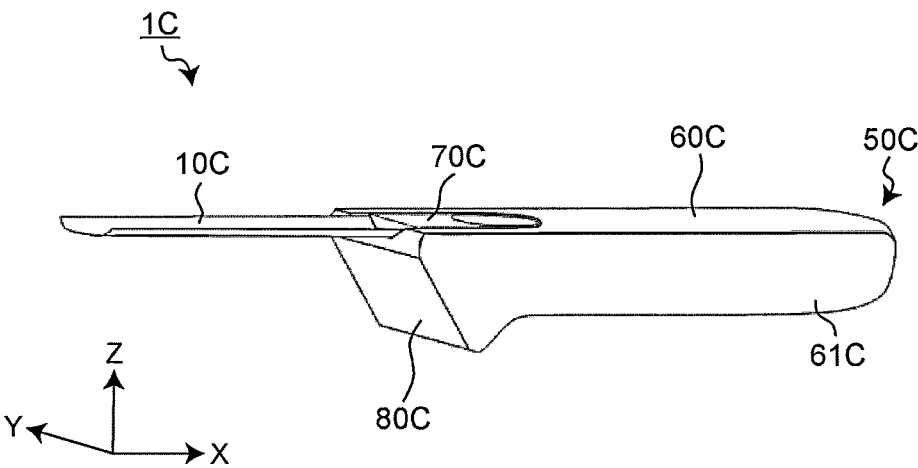
FIG. 14A is a schematic perspective view of an example of an oral device of Embodiment 3 according to an exemplary aspect.
Figure 14B:
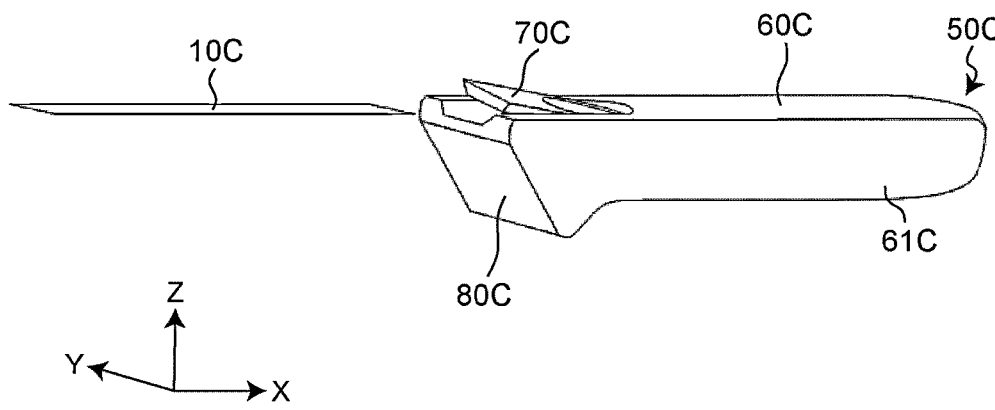
FIG. 14B is a schematic perspective view of an example of the oral device of Embodiment 3 according to an exemplary aspect.

An example of the oral device of Embodiment 3 will be described with reference to FIG. 14A and FIG. 14B. FIG. 14A and FIG. 14B are schematic perspective views of an example of an oral device 1C of Embodiment 3 according to the exemplary aspect. Note that in FIG. 14A and FIG. 14B, the display of the display unit 90 is omitted.

Embodiment 3 is different from Embodiment 1 in that a direction in which a body portion 60C of an oral body device 50C extends is the same as the attachment/detachment direction of an oral appliance 10C, and that the oral appliance 10C is attached, in a deformed state, to an attachment/detachment operation unit 70C.

As illustrated in FIG. 14A and FIG. 14B, the body portion 60C of the oral body device 50C is formed of a rod-shaped member extending in the same direction as the attachment/detachment direction of the oral appliance 10C. The attachment/detachment direction of the oral appliance 10C is the X direction in FIG. 14A and FIG. 14B.

A guard 80C is formed by a convex portion that protrudes in a direction intersecting the attachment/detachment direction of the oral appliance 10C. The guard 80C is provided on the side opposite to the side on which the attachment/detachment operation unit 70C is provided in the body portion 60C. The guard 80C protrudes to the outer side portion relative to a grip portion 61C. In addition, an inclined surface that suppresses liquid such as saliva from flowing toward the grip portion 61C is formed on the guard 80C. Accordingly, saliva can be prevented from flowing to the grip portion 61C.

The oral appliance 10C is formed in a sheet shape that is deformable in the longitudinal direction. In Embodiment 3, the entire oral appliance 10C has flexibility. That is, in the oral appliance 10C, the functional portion 20, the wiring portion 30, and the connection portion 40 have flexibility. The oral appliance 10C is attached, in a deformed state, to the attachment/detachment operation unit 70C.

Figure 15A:
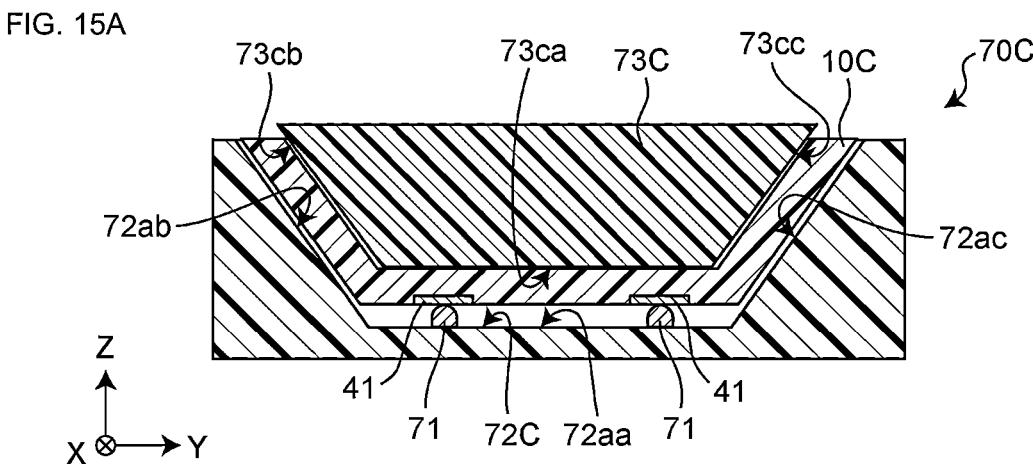
FIG. 15A is a schematic partially enlarged cross-sectional view illustrating an example of an oral appliance attached to an attachment/detachment operation unit in an enlarged manner.
Figure 15B:
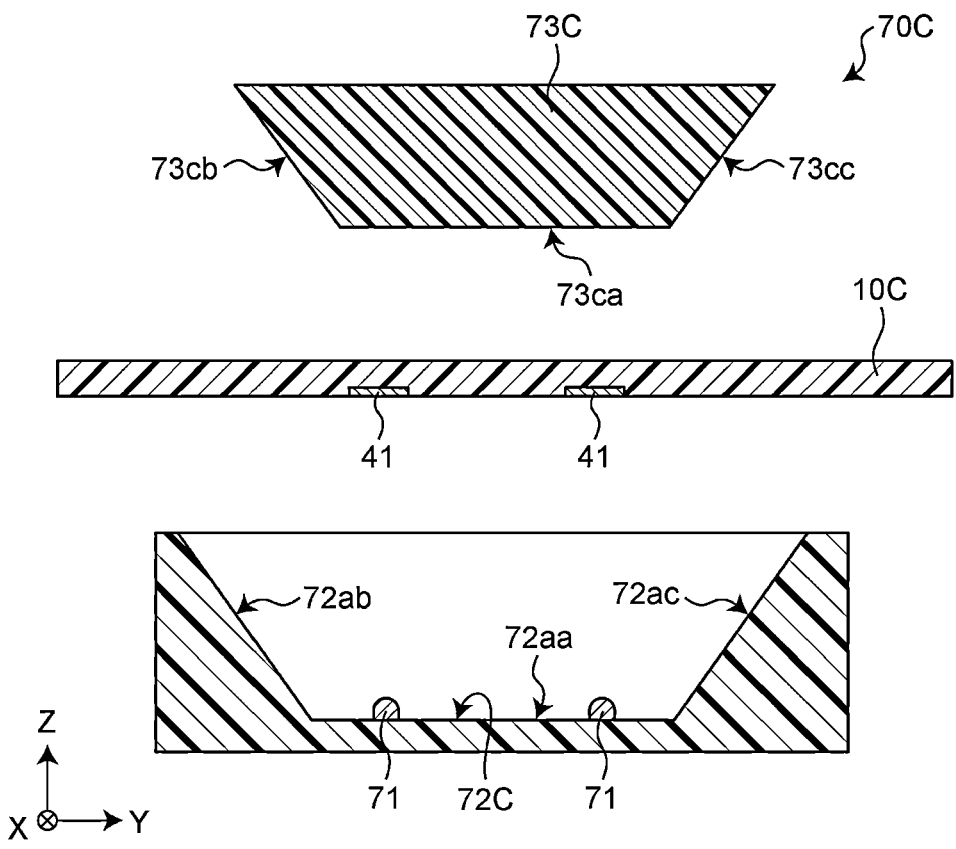
FIG. 15B is a schematic exploded cross-sectional view of the attachment/detachment operation unit of FIG. 15A.

FIG. 15A is a schematic partially enlarged cross-sectional view illustrating an example of the oral appliance 10C attached to the attachment/detachment operation unit 70C in an enlarged manner. FIG. 15B is a schematic exploded cross-sectional view of the attachment/detachment operation unit 70C of FIG. 15A. Note that FIG. 15A and FIG. 15B are cross-sectional views of the oral appliance 10C and the attachment/detachment operation unit 70C taken along a YZ plane.

As illustrated in FIG. 15A and FIG. 15B, the attachment/detachment operation unit 70C includes an arrangement surface 72C that is curved in a concave shape or a convex shape, and a pressing member 73C that is curved in a concave shape or a convex shape along the shape of the arrangement surface 72C.

The arrangement surface 72C is formed to be curved in a concave shape. To be specific, the arrangement surface 72C is formed to be recessed in a trapezoidal shape. The arrangement surface 72C includes a flat bottom surface 72aa and a plurality of inclined surfaces 72ab and 72ac extending at an angle toward the bottom surface 72aa. The plurality of connection terminals 71 is arranged on the bottom surface 72aa of the arrangement surface 72C.

The pressing member 73C is formed so as to be convexly curved along the shape of the arrangement surface 72C. Specifically, the pressing member 73C is formed in a trapezoidal shape. The pressing member 73C includes a flat bottom surface 73ca and a plurality of inclined surfaces 73cb and 73cc inclined and extending toward the bottom surface 73ca.

As illustrated in FIG. 15A, the oral appliance 10C is attached to the attachment/detachment operation unit 70C by being pressed by the pressing member 73C. The oral appliance 10C is fixed in a state of being deformed along the shapes of the pressing member 73C and the arrangement surface 72C by being sandwiched between the pressing member 73C and the arrangement surface 72C. In Embodiment 3, the oral appliance 10C is deformed into a trapezoidal shape protruding downward in the Z direction.

To be specific, the oral appliance 10C is sandwiched between the bottom surface 72aa of the arrangement surface 72C and the bottom surface 73ca of the pressing member 73C, between the inclined surface 72ab of the arrangement surface 72C and the inclined surface 73cb of the pressing member 73C, and between the inclined surface 72ac of the arrangement surface 72C and the inclined surface 73cc of the pressing member 73C.

The plurality of electrodes 41 of the oral appliance 10C is electrically connected to the plurality of connection terminals 71 arranged on the bottom surface 72aa of the arrangement surface 72C by physically contacting the plurality of connection terminals 71.

Thus, the oral appliance 10C is deformed into a trapezoidal shape in the exemplary aspect and fixed to the attachment/detachment operation unit 70C.

[Effects]

According to the oral appliance 10C according to Embodiment 3, the following effects can be achieved.

In the oral appliance 10C, the functional portion 20, the wiring portion 30, and the connection portion 40 have flexibility. Therefore, the oral appliance 10C is fixed in a state of being deformed along the shape of the attachment/detachment operation unit 70C. Thus, the oral appliance 10C can be suppressed from hanging down. For example, when saliva or the like adheres to the oral appliance 10C, the oral appliance 10C may hang down due to the weight of the saliva. By deforming the oral appliance 10C into a trapezoidal shape or the like to be attached, the oral appliance 10C can be suppressed from hanging down while maintaining the deformed shape of the oral appliance 10C. Meanwhile, when the oral appliance 10C is used in the oral cavity, the oral appliance 10C can be deformed along the shape of the contact site in the oral cavity. This configuration improves the measurement accuracy or radiation accuracy.

Note that in Embodiment 3, an example in which the entire oral appliance 10C has a flexibility has been described, but the present invention is not limited thereto. The oral appliance 10C may be stably fixed in a deformed state when being attached to the attachment/detachment operation unit 70C, and a part of the oral appliance 10C may be formed of a member having no flexibility.

In Embodiment 3, an example in which the oral appliance 10C is deformed into a trapezoidal shape protruding downward has been described, but the exemplary aspects of the present invention are not limited thereto. For example, the oral appliance 10C may be deformed into a concave shape or a convex shape when viewed from the X direction.

Figure 16A:
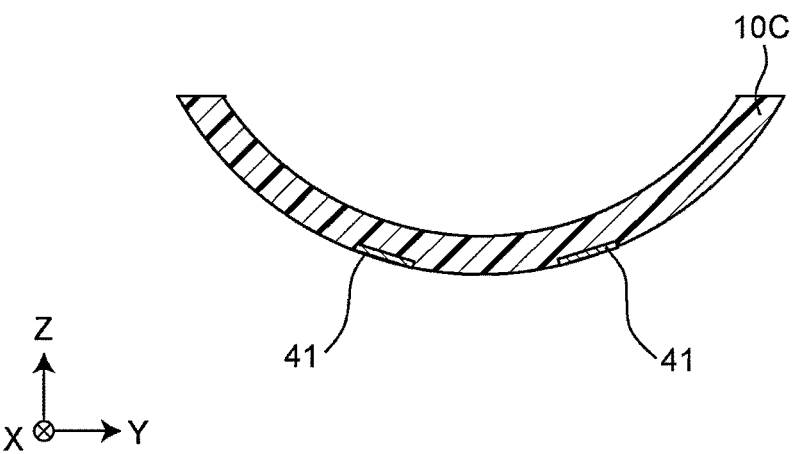
FIG. 16A is a schematic enlarged cross-sectional view illustrating an example of variation of the oral appliance in an enlarged manner.
Figure 16B:
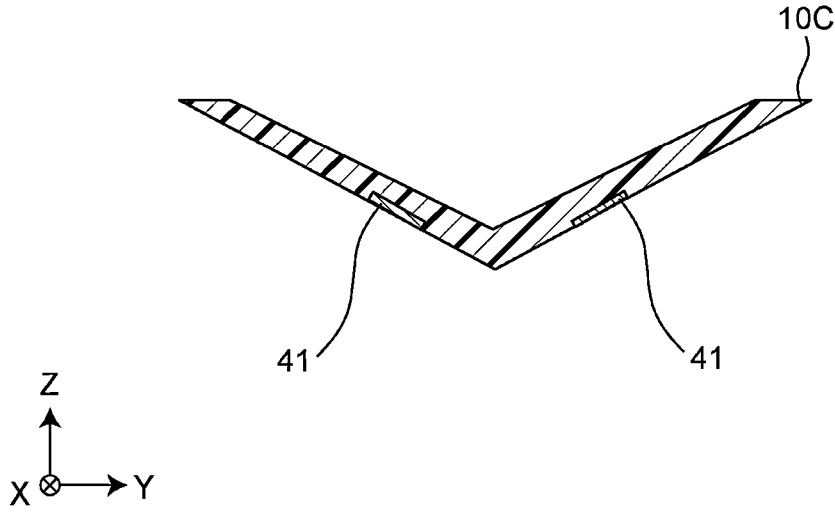
FIG. 16B is a schematic enlarged cross-sectional view illustrating an example of variation of the oral appliance in an enlarged manner.
Figure 16C:
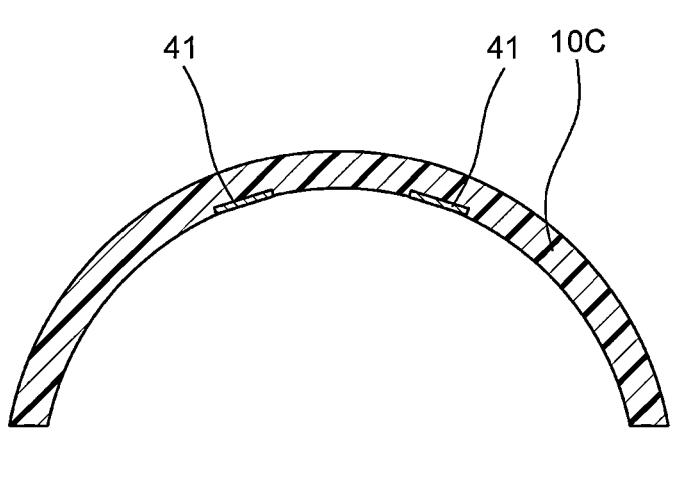
FIG. 16C is a schematic enlarged cross-sectional view illustrating an example of variation of the oral appliance in an enlarged manner.
Figure 16C:
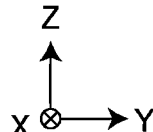

FIGS. 16A to 16C are a schematic enlarged cross-sectional view illustrating an example of variation of the oral appliance 10C in an enlarged manner. Note that FIGS. 16A to 16C illustrate a cross-sectional view of the connection portion 40 of the oral appliance 10C taken along the YZ plane. As illustrated in FIG. 16A, the oral appliance 10C may be deformed into a U-shape protruding downward when viewed from the X direction. As illustrated in FIG. 16B, the oral appliance 10C may be deformed into a V-shape protruding downward when viewed from the X direction. As illustrated in FIG. 16C, the oral appliance 10C may be deformed into a U-shape protruding upward when viewed from the X direction. Also in these configurations, the oral appliance 10C can be suppressed from hanging down.

Embodiment 4

An oral appliance according to Embodiment 4 of an exemplary aspect will be described. Note that in Embodiment 4, differences from Embodiment 1 will be mainly described. In Embodiment 4, configurations identical or equivalent to those in Embodiment 1 are denoted by the same reference numerals to be described. Further, in Embodiment 4, the description overlapping with Embodiment 1 will be omitted.

Figure 17:
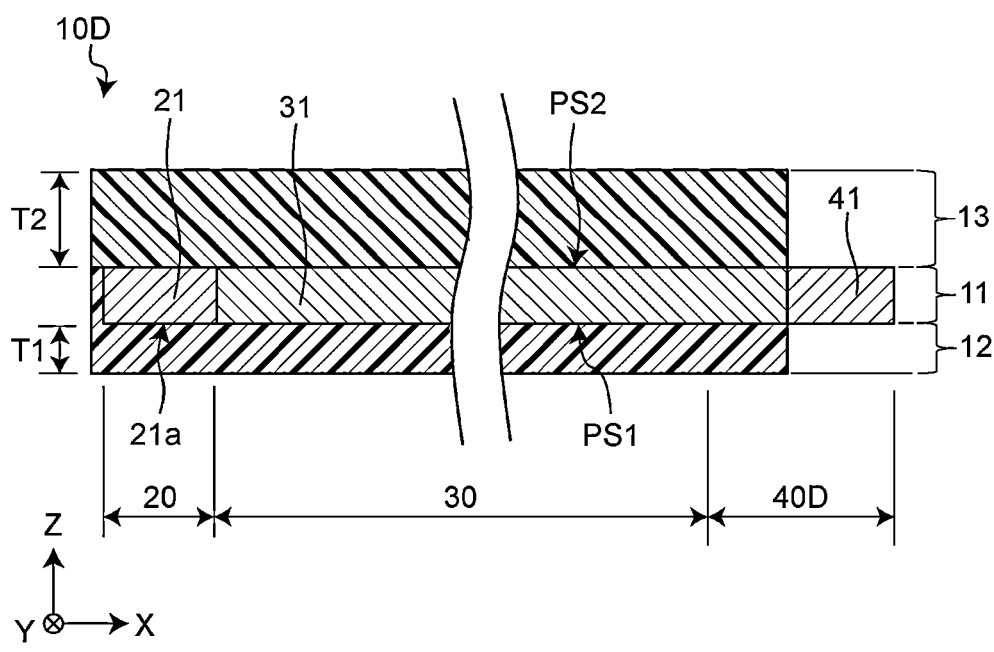
FIG. 17 is a schematic partially enlarged cross-sectional view illustrating an example of an oral appliance of Embodiment 4 according to an exemplary aspect in an enlarged manner.

An example of the oral appliance of Embodiment 4 will be described with reference to FIG. 17. FIG. 17 is a schematic partially enlarged cross-sectional view illustrating an example of an oral appliance 10D of Embodiment 4 according to the present invention in an enlarged manner.

Embodiment 4 is different from Embodiment 1 in that the electrode 41 is exposed from both the first insulating layer 12 and the second insulating layer 13.

As illustrated in FIG. 17, in a connection portion 40D of the oral appliance 10D, the electrode 41 is exposed from both the first insulating layer 12 and the second insulating layer 13.

[Effects]

According to the oral appliance 10D according to Embodiment 4, the following effects can be achieved.

In the oral appliance 10C, the electrode 41 is exposed from both the first insulating layer 12 and the second insulating layer 13. With such a configuration, the degree of freedom in attachment of the oral appliance 10C can be increased. For example, in the attachment/detachment operation unit 70, in a case where the connection terminal 71 is provided on the arrangement surface 72, the electrode 41 of the oral appliance 10D can physically come into contact with the connection terminal 71 on the first main surface PS1 side. In the attachment/detachment operation unit 70, in a case where the connection terminal 71 is provided at the pressing member 73, the electrode 41 of the oral appliance 10D can physically come into contact with the connection terminal 71 on the second main surface PS2 side.

Alternatively, the upper and lower surfaces of the oral appliance 10D can be interchanged and attached to the attachment/detachment operation unit 70. Accordingly, when the oral appliance 10D is attached to the attachment/detachment operation unit 70, it can be fixed with the sensor surface 21a of the sensor unit 21 facing upward or with the sensor surface 21a of the sensor unit 21 facing downward.

In this way, the electrode 41 is exposed from both the first insulating layer 12 and the second insulating layer 13, thereby increasing the degree of freedom in the attachment method of the oral appliance 10D.

Embodiment 5

An oral device according to Embodiment 5 of the present invention will be described. Note that in Embodiment 5, differences from Embodiment 1 will be mainly described. In Embodiment 5, configurations identical or equivalent to those in Embodiment 1 are denoted by the same reference numerals to be described. Further, in Embodiment 5, the description overlapping with Embodiment 1 will be omitted.

Figure 18:
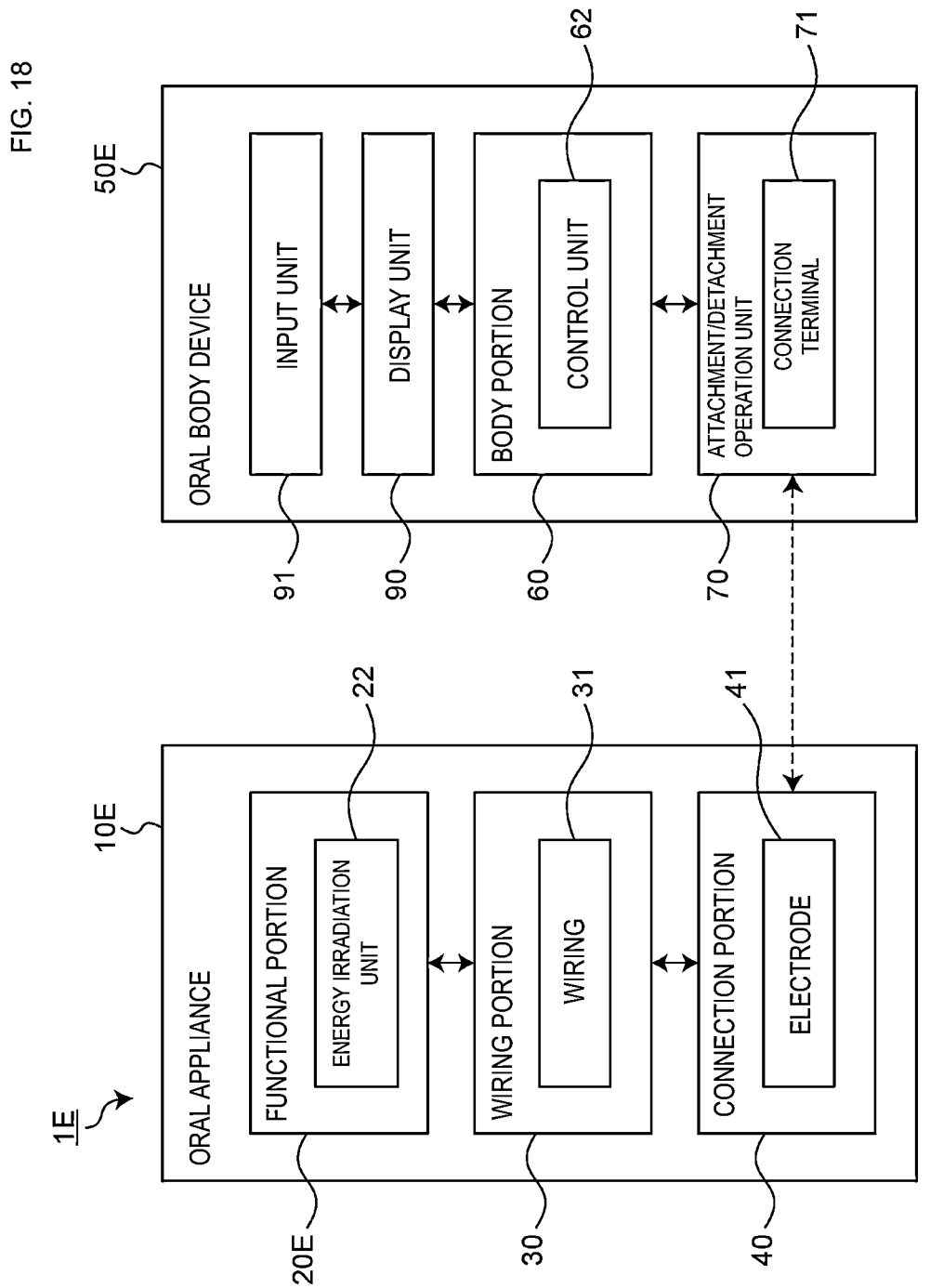
FIG. 18 is a block diagram illustrating a main configuration of an example of an oral device of Embodiment 5 according to an exemplary aspect.

An example of the oral device of Embodiment 5 will be described with reference to FIG. 18. FIG. 18 is a block diagram illustrating a main configuration of an example of an oral device 1E of Embodiment 5 according to the present invention.

Embodiment 5 is different from Embodiment 1 in that a functional portion 20E of an oral appliance 10E has the energy irradiation unit 22 and that an oral body device 50E controls the energy irradiation unit 22.

As illustrated in FIG. 18, in the oral appliance 10E, the functional portion 20E has the energy irradiation unit 22 that radiates energy into the oral cavity. In Embodiment 5, an example in which the oral appliance 10E is a laser treatment device will be described. The oral appliance 10E is detachably attached to the oral body device 50E to be used.

Figure 19A:
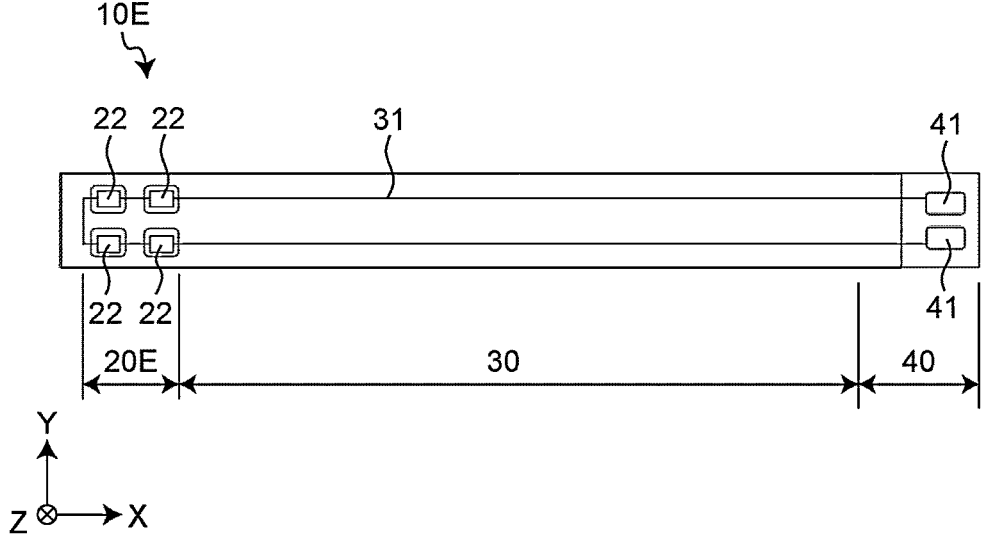
FIG. 19A is a schematic view illustrating an example of an oral appliance.
Figure 19B:
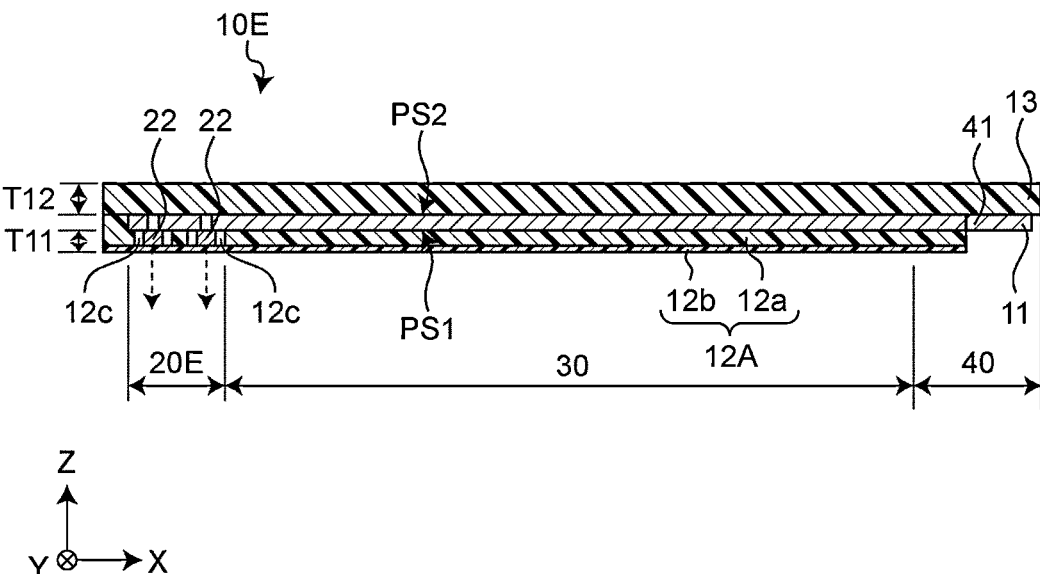
FIG. 19B is a schematic cross-sectional view of the example of the oral appliance of FIG. 19A.

FIG. 19A is a schematic view illustrating an example of the oral appliance 10E. FIG. 19B is a schematic cross-sectional view of the example of the oral appliance 10E of FIG. 19A. As illustrated in FIG. 19A and FIG. 19B, the functional portion 20E has a plurality of the energy irradiation units 22. In Embodiment 5, the functional portion 20E includes four energy irradiation units 22.

The plurality of energy irradiation units 22 is, for example, a vertical cavity surface emitting laser (VCSEL). The plurality of energy irradiation units 22 is mounted on the first main surface PS1 of the wiring layer 11, which is covered with a first insulating layer 12A. The first insulating layer 12A includes an insulator 12a arranged on the first main surface PS1 of the wiring layer 11 and a transparent resin film 12b attached to the insulator 12a. The insulator 12a is provided with a plurality of holes 12c for accommodating the plurality of energy irradiation units 22. In the functional portion 20E, the resin film 12b closes the plurality of holes 12c provided in the insulator 12a. The laser beams from the plurality of energy irradiation units 22 are transmitted through the resin film 12b of the first insulating layer 12A and radiated to an irradiation site in the oral cavity.

The functional portion 20E has flexibility. Therefore, the functional portion 20E can be deformed along the shape of the irradiation site in the oral cavity.

A thickness T11 of the first insulating layer 12A in the functional portion 20E is smaller than the thickness T12 of the second insulating layer 13. The thickness T11 of the first insulating layer 12A in the functional portion 20E is equal to or less than $\frac{1}{2}$ times the thickness T12 of the second insulating layer 13. Preferably, the thickness T11 of the first insulating layer 12A in the functional portion 20E is equal to or less than $\frac{1}{8}$ times the thickness T12 of the second insulating layer 13. Accordingly, the irradiation efficiency of the laser beams of the energy irradiation unit 22 can be improved.

Returning to FIG. 18, the oral body device 50E includes an input unit 91. The input unit 91 acquires input information for operating the energy irradiation unit 22. The user inputs input information to the input unit 91. For example, the input unit 91 may be one or a plurality of operation buttons, a touch panel, a microphone, or the like. The input information input to the input unit 91 is transmitted to the control unit 62. Examples of the input information include laser irradiation, laser shutdown, timer, output value, and the like.

The control unit 62 receives input information from the input unit 91 and controls the motion of the oral appliance 10E based on the input information. The control unit 62 controls the plurality of energy irradiation units 22 based on the input information. For example, when input information of laser irradiation is input to the input unit 91, the control unit 62 controls the plurality of energy irradiation units 22 of the oral appliance 10E and causes the plurality of energy irradiation units 22 to radiate laser beams.

[Effects]

According to the oral appliance 10E according to Embodiment 5, the following effects can be achieved.

In the oral appliance 10E, the functional portion 20E includes the energy irradiation unit 22 that radiates energy into the oral cavity. With such a configuration, the energy can be radiated to the irradiation site in the oral cavity.

The functional portion 20E has flexibility according to the exemplary aspect. Accordingly, the functional portion 20E can be deformed along the shape of the irradiation site in the oral cavity, and can appropriately come into contact with the irradiation site.

The energy irradiation unit 22 is arranged on the first main surface PS1 side of the wiring layer 11. In the functional portion 20E, the thickness T11 of the first insulating layer 12A is smaller than the thickness T12 of the second insulating layer 13. Accordingly, the irradiation efficiency of the laser beams of the energy irradiation unit 22 can be improved. By making the thickness T11 of the first insulating layer 12A smaller than the thickness T12 of the second insulating layer 13, it is possible to reduce the influence of the first insulating layer 12A on the laser irradiation from the energy irradiation unit 22. Specifically, since the distance between the energy irradiation unit 22 and the irradiation site can be reduced, the loss of the laser beams radiated from the energy irradiation unit 22 can be reduced.

Note that in Embodiment 5, an example in which the energy irradiation unit 22 is a vertical cavity surface emitting laser has been described, but the exemplary aspects of the present invention are not limited thereto. It is sufficient that the energy irradiation unit 22 can radiate energy.

In Embodiment 5, an example in which the functional portion 20E includes four energy irradiation units 22 has been described, but the present invention is not limited thereto. The functional portion 20E only needs to have one or the plurality of energy irradiation units 22.

(Modification 3)

Figure 20A:
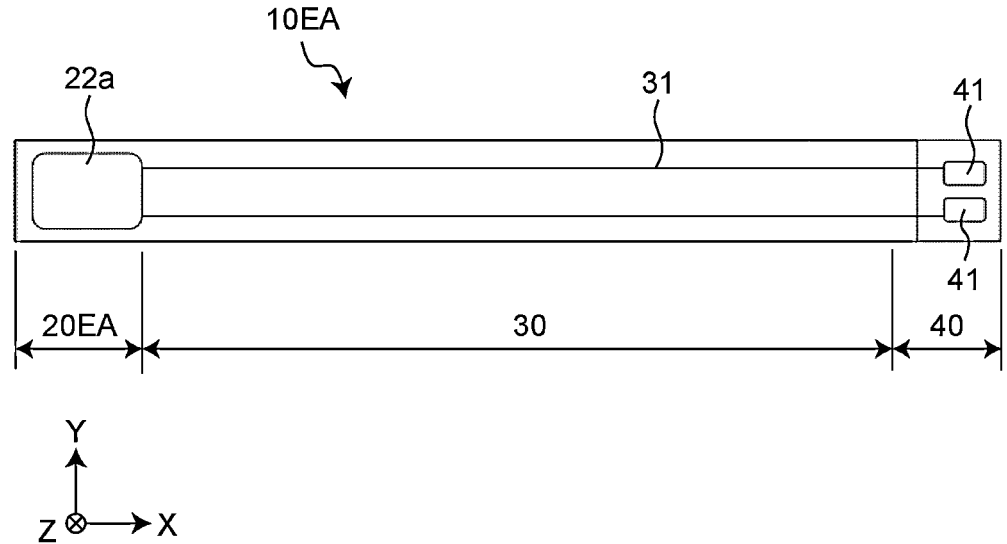
FIG. 20A is a schematic view illustrating an oral appliance of Modification 3 according to an exemplary aspect.
Figure 20B:
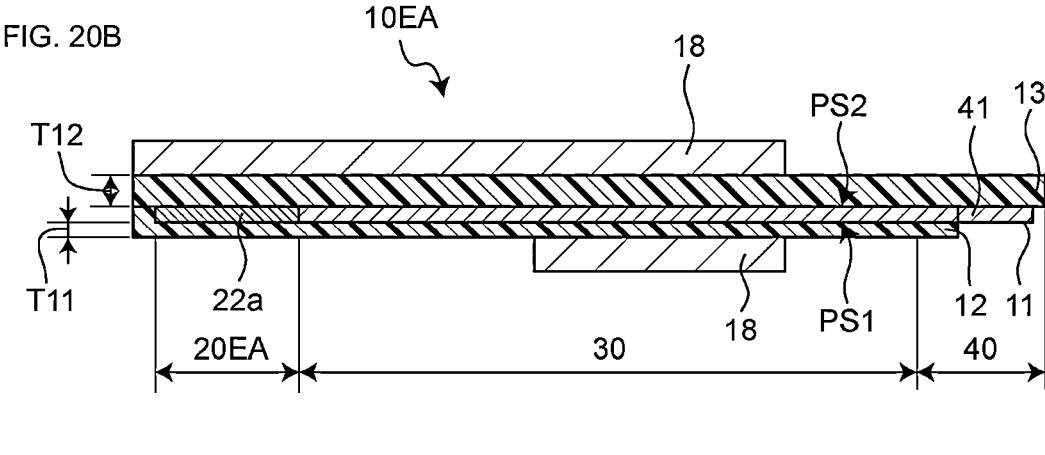
FIG. 20B is a schematic cross-sectional view of the oral appliance of Modification 3 of FIG. 20A.
Figure 20B:
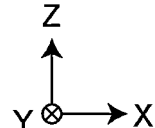

FIG. 20A is a schematic view illustrating an oral appliance 10EA of Modification 3. FIG. 20B is a schematic cross-sectional view of the oral appliance 10EA of Modification 3 of FIG. 20A. As illustrated in FIG. 20A and FIG. 20B, the oral appliance 10EA is used as a hyperthermia device. An energy irradiation unit 22*a* of a functional portion 20EA is a seat heater. A seat heater performs heating by using heat generated by a resistor. Further, the oral appliance 10EA may be covered with a heat insulating material 18 except for a portion heated by the energy irradiation unit 22*a*. In the oral appliance 10EA, the first main surface PS1 side of the wiring layer 11 is not covered with the heat insulating material 18.

Embodiment 6

An oral device according to Embodiment 6 of an exemplary aspect will be described. Note that in Embodiment 6, differences from Embodiment 1 will be mainly described. In Embodiment 6, configurations identical or equivalent to those in Embodiment 1 are denoted by the same reference numerals to be described. Further, in Embodiment 6, the description overlapping with Embodiment 1 will be omitted.

Figure 21:
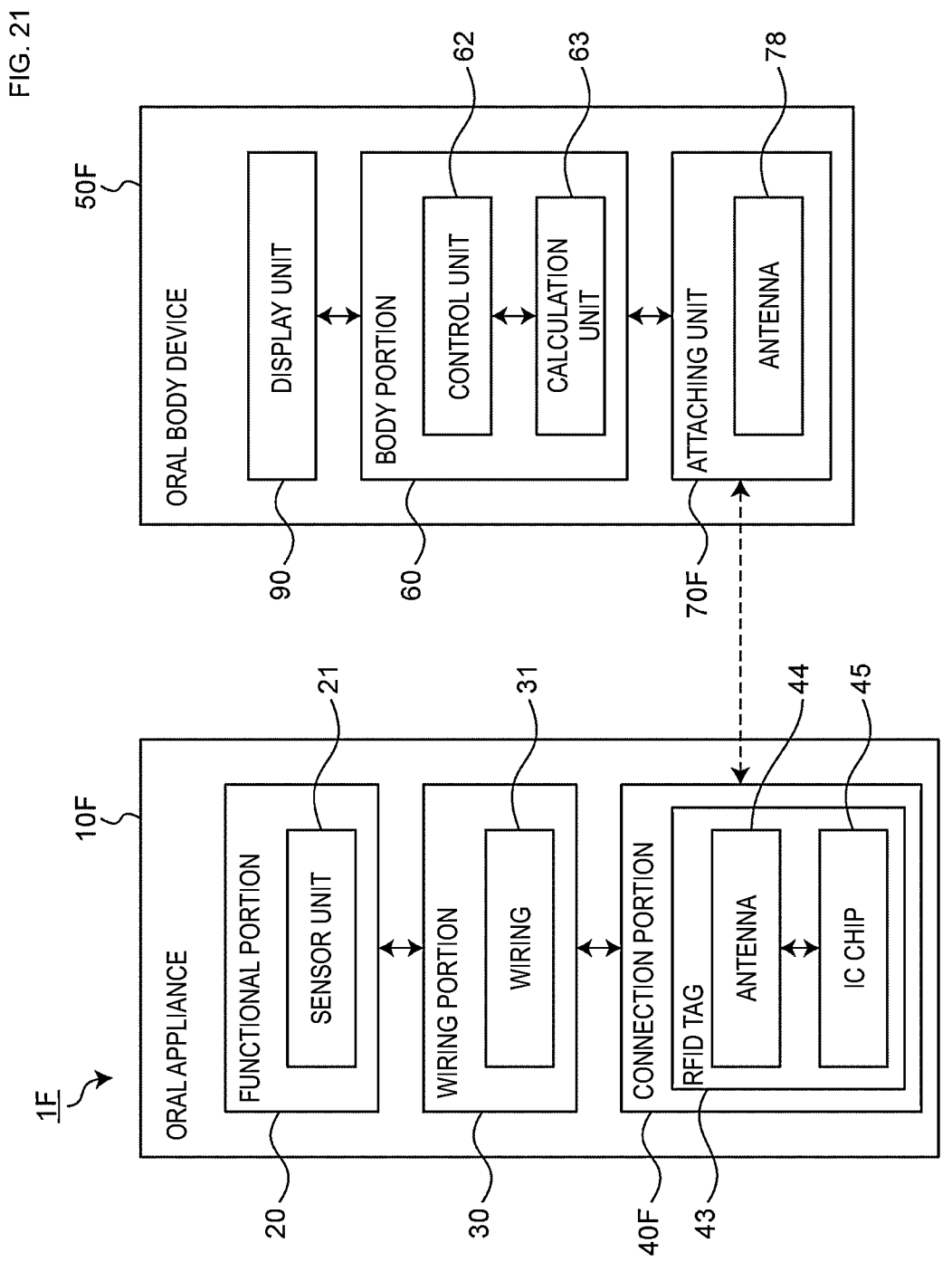
FIG. 21 is a block diagram illustrating a main configuration of an example of an oral device of Embodiment 6 according to an exemplary aspect.

An example of the oral device of Embodiment 6 will be described with reference to FIG. 21. FIG. 21 is a block diagram illustrating a main configuration of an example of an oral device 1F of Embodiment 6 according to the exemplary aspect.

Embodiment 6 is different from Embodiment 1 in that an electrical connection portion of an oral appliance 10F is a radio frequency identification (RFID) tag 43, and an electrical connection conductor of an oral body device 50F is an antenna 78.

As illustrated in FIG. 21, in the oral appliance 10F, a connection portion 40F has the RFID tag 43 as an electrical connection portion. The RFID tag 43 is electrically connected to the electrical connection conductor of the oral body device 50F by wireless connection. That is, the RFID tag 43 is electrically connected to the antenna 78 of the oral body device 50F in a non-contact manner.

Figure 22:
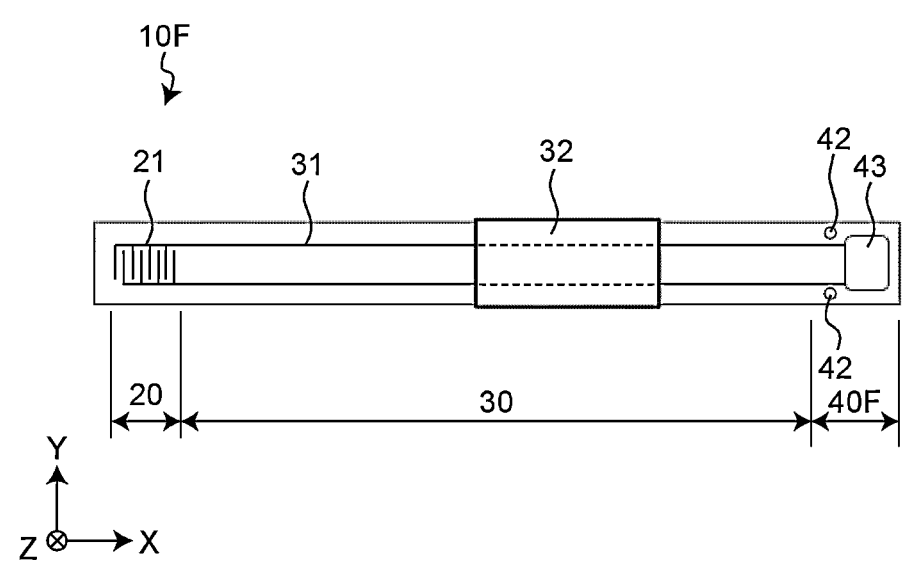
FIG. 22 is a schematic view illustrating an example of an oral appliance.
Figure 23:
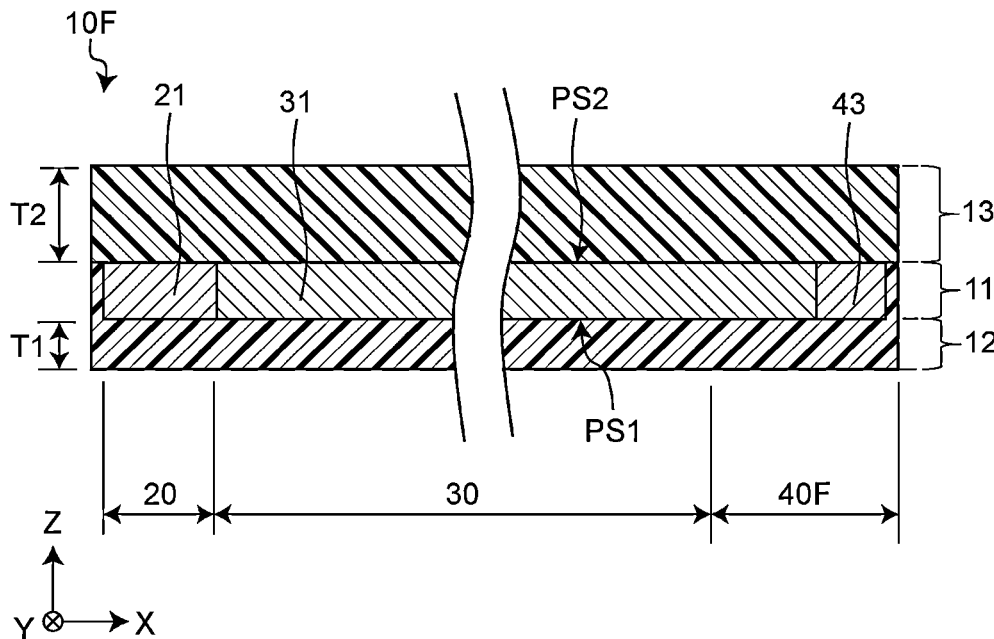
FIG. 23 is a schematic cross-sectional view of an example of the oral appliance of FIG. 22.

FIG. 22 is a schematic view illustrating an example of the oral appliance 10F. FIG. 23 is a schematic cross-sectional view of an example of the oral appliance 10F of FIG. 22. As illustrated in FIG. 22 and FIG. 23, the RFID tag 43 is arranged in a connection portion 40F in the wiring layer 11. The RFID tag 43 is covered with the plurality of insulating layers 12 and 13. That is, the RFID tag 43 is not exposed from the plurality of insulating layers 12 and 13.

Figure 24:
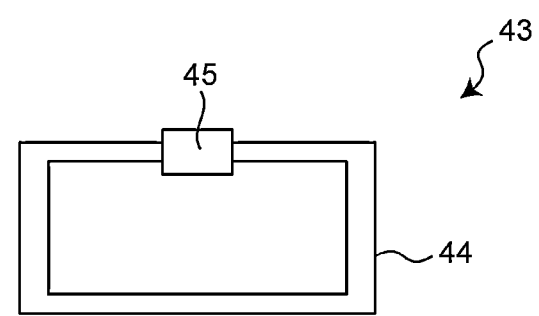
FIG. 24 is a schematic view of an example of an RFID tag.

FIG. 24 is a schematic view of an example of the RFID tag 43. As illustrated in FIG. 24, the RFID tag 43 includes an antenna 44 and an IC chip 45 connected to the antenna 44.

The antenna 44 is formed by a conductive linear member wound into a coil shape. The antenna 44 is formed of, for example, a wiring conductor pattern.

The IC chip 45 is, for example, a packaged RFIC chip (e.g., a bare chip) having input/output terminals. For example, the IC chip 45 is an IC chip on which an RF circuit for RFID tag, a memory circuit, a control circuit, and the like are mounted. The IC chip 45 is connected to the sensor unit 21 of the functional portion 20 via the wiring 31.

Figure 25:
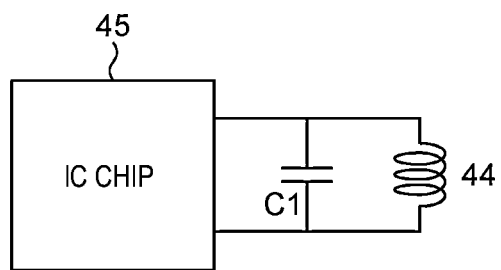
FIG. 25 is a schematic circuit diagram of an example of the RFID tag.

FIG. 25 is a schematic circuit diagram of an example of the RFID tag 43. As illustrated in FIG. 25, the antenna 44 is connected to the IC chip 45. A chip capacitor C1 is connected in parallel to the antenna 44. The chip capacitor C1 is, for example, a multilayer ceramic chip component. An antenna resonant circuit having a resonant frequency is configured by the antenna 44, the chip capacitor C1, and the capacitance component of the IC chip 45 itself. Note that this circuit is an example, and the resonant circuit of the RFID tag 43 is not limited thereto.

Figure 26:
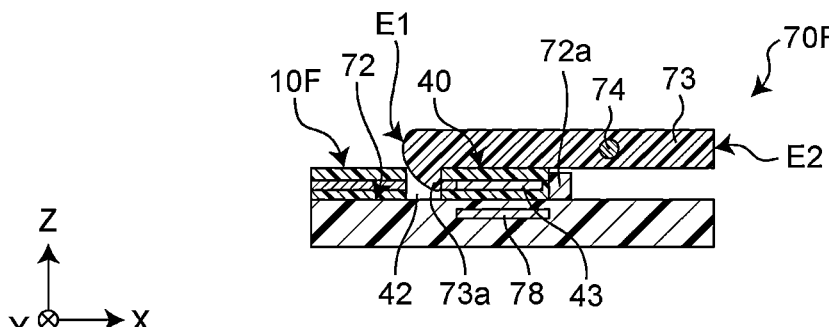
FIG. 26 is a schematic partially enlarged cross-sectional view illustrating an example of the oral appliance attached to an attachment/detachment operation unit in an enlarged manner.

FIG. 26 is a schematic partially enlarged cross-sectional view illustrating an example of the oral appliance 10F attached to an attachment/detachment operation unit 70F in an enlarged manner. FIG. 26 illustrates a state in which the oral appliance 10F is attached to the attachment/detachment operation unit 70F, and the oral appliance 10F and the body device 50F are electrically connected in a non-contact manner.

As illustrated in FIG. 26, the attachment/detachment operation unit 70F includes the antenna 78. In this specification, the antenna 78 may be referred to as the body side antenna 78. Note that the attachment/detachment operation unit 70F has the same configuration as that of the attachment/detachment operation unit 70 of Embodiment 1 except that the attachment/detachment operation unit 70F includes the antenna 78 instead of the connection terminal 71.

In the exemplary aspect, the body side antenna 78 is formed by a conductive linear member wound in a coil shape. The body side antenna 78 is formed, for example, a wiring conductor pattern.

The body side antenna 78 is housed inside the body device 50F. The body side antenna 78 is arranged under the arrangement surface 72. To be specific, in a state in which the oral appliance 10F is arranged on the arrangement surface 72 and attached to the attachment/detachment operation unit 70F, the body side antenna 78 is positioned under the antenna 44 of the RFID tag 43. That is, in a state in which the oral appliance 10F is arranged on the arrangement surface 72 and attached to the attachment/detachment operation unit 70F, the body side antenna 78 faces the antenna 44 of the RFID tag 43.

When the antenna 44 of the oral appliance 10F and the body side antenna 78 of the body device 50 face each other, the RFID tag 43 and the body side antenna 78 are magnetic-field coupled to each other. As such, an induced current flows through the antenna 44, and the IC chip 45 operates. Thus, the oral appliance 10F can be used.

[Effects]

According to the oral appliance 10F according to Embodiment 6, the following effects can be achieved.

The electrical connection portion of the oral appliance 10F is the RFID tag 43. The electrical connection conductor of the oral body device 50F is the antenna 78. The oral appliance 10F is electrically connected by making a wireless connection between the RFID tag 43 and the antenna 78 of the oral body device 50F. With such a configuration, the electrical connection between the oral appliance 10F and the oral body device 50F can be easily performed.

Embodiment 7

An oral appliance according to Embodiment 7 of an exemplary aspect will be described. Note that in Embodiment 7, differences from Embodiment 1 will be mainly described. In Embodiment 7, configurations identical or equivalent to those in Embodiment 1 are denoted by the same reference numerals to be described. Further, in Embodiment 7, the description overlapping with Embodiment 1 will be omitted.

Figure 27:
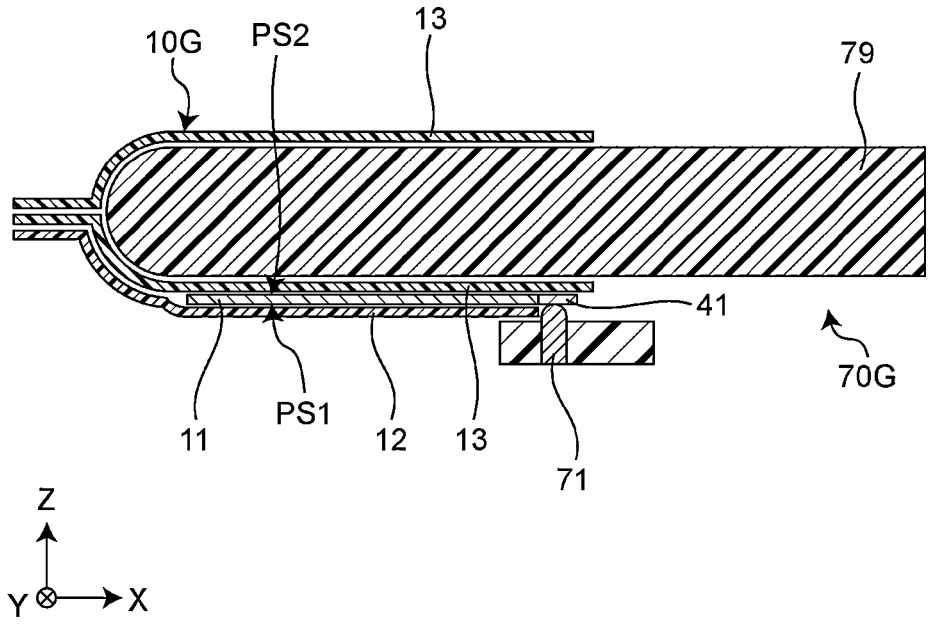
FIG. 27 is a schematic cross-sectional view illustrating an example of an oral appliance of Embodiment 7 according to an exemplary aspect in an enlarged manner.

An example of the oral appliance of Embodiment 7 will be described with reference to FIG. 27. FIG. 27 is a schematic cross-sectional view illustrating an example of an oral appliance 10G of Embodiment 7 according to the exemplary aspect in an enlarged manner. Note that FIG. 27 illustrates an example of a state in which the oral appliance 10G is attached to an attachment/detachment operation unit 70G.

Embodiment 7 is different from Embodiment 1 in that the oral appliance 10G is configured in a bag shape.

As illustrated in FIG. 27, the oral appliance 10G is configured in the bag shape in which the first main surface PS1 of the wiring layer 11 is arranged to face outward and the second main surface PS2 of the wiring layer is arranged to face inward. Specifically, the oral appliance 10G is configured in the bag shape having an opening at one end.

The attachment/detachment operation unit 70G has a columnar member 79 to which the oral appliance 10G is attached. The columnar member 79 is formed in a cylinder shape. In addition, a tip of the columnar member 79 is formed in a hemispherical shape.

The oral appliance 10G is caused to cover the columnar member 79 and thereby is attached to the attachment/detachment operation unit 70G. In addition, when the oral appliance 10G is caused to cover the columnar member 79, the electrode 41 of the oral appliance 10G is electrically connected to the connection terminal 71 of the attachment/detachment operation unit 70G.

[Effects]

According to the oral appliance 10G according to Embodiment 7, the following effects can be achieved.

The oral appliance 10G is configured in a bag shape in which the first main surface PS1 of the wiring layer 11 is arranged to face outward and the second main surface PS2 of the wiring layer 11 is arranged to face inward. Also in such a configuration, the oral appliance 10G can be attached to the attachment/detachment operation unit 70G. In addition, the oral appliance 10G can be more firmly fixed to the oral body device.

Embodiment 8

An oral appliance according to Embodiment 8 of an exemplary aspect will be described. Note that in Embodiment 8, differences from Embodiment 1 will be mainly described. In Embodiment 8, configurations identical or equivalent to those in Embodiment 1 are denoted by the same reference numerals to be described. Further, in Embodiment 8, the description overlapping with Embodiment 1 will be omitted.

Figure 28A:
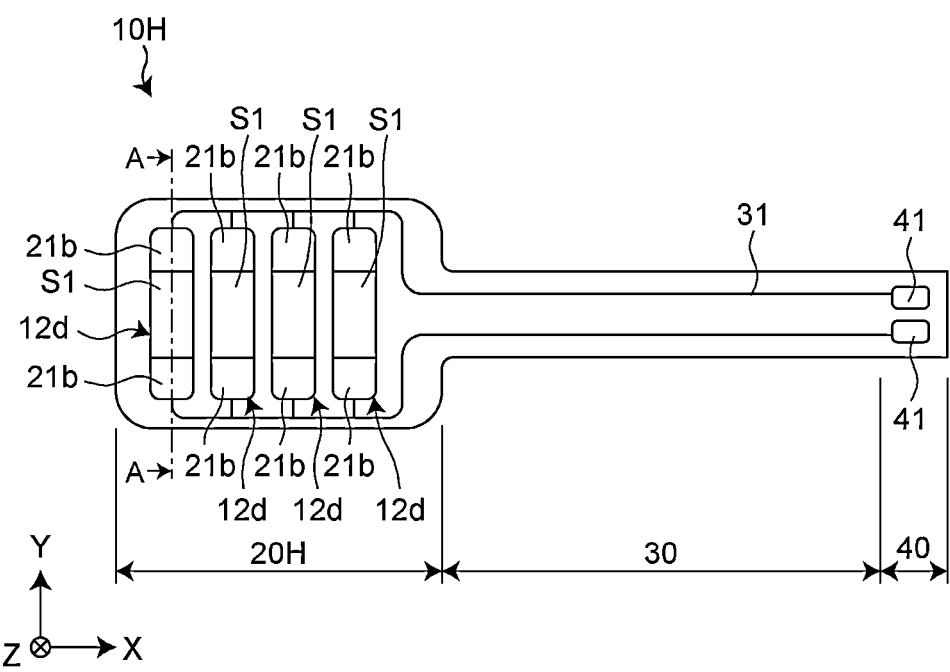
FIG. 28A is a schematic view illustrating an example of an oral appliance of Embodiment 8 according to an exemplary aspect.
Figure 28B:
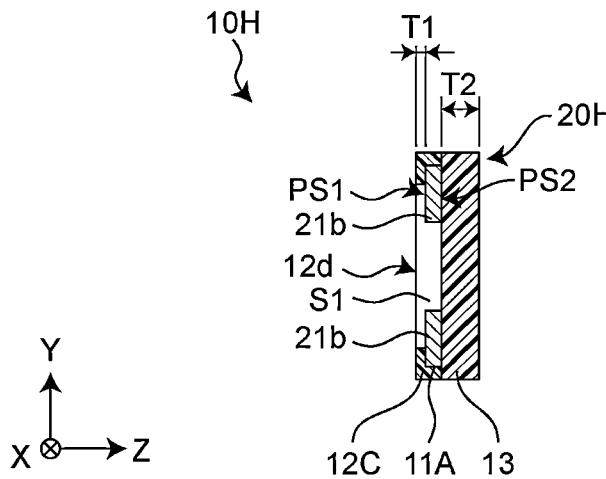
FIG. 28B is a schematic cross-sectional view of the oral appliance of FIG. 28A taken along line A-A.

An example of the oral appliance of Embodiment 8 will be described with reference to FIG. 28A and FIG. 28B. FIG. 28A is a schematic cross-sectional view illustrating an example of an oral appliance 10H of Embodiment 8 according to the exemplary aspect in an enlarged manner. FIG. 28B is a schematic cross-sectional view of the oral appliance 10H of FIG. 28A taken along line A-A.

Embodiment 8 is different from Embodiment 1 in that a plurality of openings 12d is provided in a first insulating layer 12C in a functional portion 20H, and a plurality of sensor units 21b is exposed from the plurality of openings 12d.

As illustrated in FIG. 28A and FIG. 28B, in the functional portion 20H of the oral appliance 10H, the plurality of openings 12d is provided in the first insulating layer 12C. The plurality of sensor units 21b is arranged in regions exposed from the plurality of openings 12d. The region exposed from the plurality of openings 12d is a portion exposed from the plurality of openings 12d when the oral appliance 10H is viewed from the first main surface PS1 side of the wiring layer 11 in the Z direction. In other words, the plurality of sensor units 21b is arranged in the plurality of openings 12d. In the plurality of openings 12d, two or more adjacent sensor units 21b among the plurality of sensor units 21b are arranged away from each other with a space S1.

The plurality of sensor units 21b is located inside the outer surface of the first insulating layer 12C. In addition, a part of sensor surfaces of the plurality of sensor units 21b is covered with the first insulating layer 12C. Therefore, a step 12da is formed by a part of the first insulating layer 12C arranged on the sensor surface of the plurality of sensor units 21b. To be specific, the step 12da is formed by a portion defining the opening 12d in the first insulating layer 12C.

In Embodiment 8, four openings 12d are provided in the first insulating layer 12C. Two sensor units 21b are arranged in each of the regions exposed from the four openings 12d. In each of the four openings 12d, two adjacent sensor units 21b are arranged away from each other with the space S1.

In other words, an insulating layer and a wiring layer are not arranged between the two adjacent sensor units 21b.

In Embodiment 8, the opening 12d is formed in a rectangular shape having a longitudinal direction in the Y direction. In other words, the opening 12d is formed in a slit shape extending in the Y direction. In addition, the four openings 12d are provided side by side in the X direction. In the opening 12d, the two adjacent sensor units 21b are arranged side by side in the Y direction.

In Embodiment 8, the plurality of sensor units 21b is impedance measurement sensors or resistance sensors and has electrodes. The electrode is formed of a plate-shaped conductive material. The electrode has, for example, a quadrangular shape when viewed from the Z direction. The electrode is formed of a corrosion-resistant material such as Au, Ag, silver chloride, Ti, Pt, or carbon. Alternatively, the electrode may be formed of, for example, Cu, Al, SUS, or the like. Moreover, the electrode may be plated in an exemplary aspect.

Figure 29:
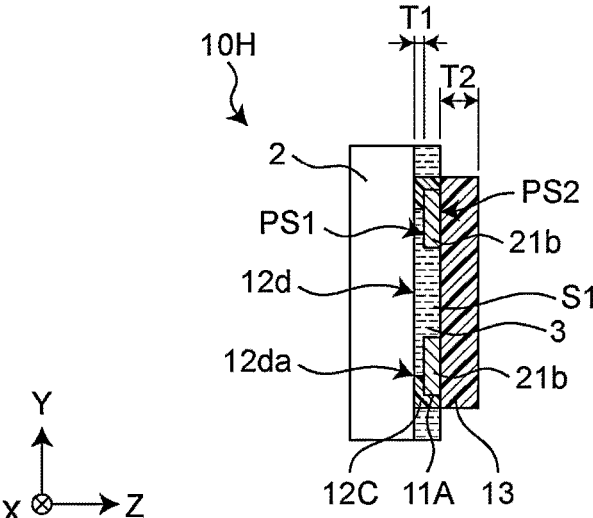
FIG. 29 is a schematic cross-sectional view illustrating an example of a state in which the oral appliance of Embodiment 8 according to an exemplary aspect is brought into contact with a measurement site.

FIG. 29 is a schematic cross-sectional view illustrating an example in which the oral appliance 10H of Embodiment 8 is brought into contact with a measurement site 2. The measurement site 2 illustrated in FIG. 29 is a tongue portion. Therefore, a saliva layer 3 is formed on the surface of the measurement site 2. The saliva layer 3 is a layer containing saliva.

As illustrated in FIG. 29, by making the thickness T1 of the first insulating layer 12C smaller than the thickness T2 of the second insulating layer 13, the height of the step 12da between the first insulating layer 12C and the sensor unit 21b can be made small. The height of the step 12da is the length in the Z direction. Therefore, when the functional portion 20H of the oral appliance 10H is brought into contact with the measurement site 2, the contact state of the plurality of sensor units 21b with respect to the measurement site 2 can be stabilized. In addition, the plurality of sensor units 21b can be arranged closer to the measurement site 2. Accordingly, the detection sensitivity of the plurality of sensor units 21b can be improved.

In addition, in a case where the saliva layer 3 is present on the surface of the measurement site 2, the measurement values acquired by the plurality of sensor units 21b vary depending on the thickness of the saliva layer 3. For example, in a case where the plurality of sensor units 21b is a resistance sensor, the resistance value tends to increase as the saliva layer 3 is thinner.

In the oral appliance 10H, the space S1 formed by the opening 12d is filled with the saliva layer 3, whereby the thickness of the saliva layer 3 in contact with the plurality of sensor units 21b can be made constant. Accordingly, the measurement values acquired by the plurality of sensor units 21 can be stabilized.

[Effects]

According to the oral appliance 10H according to Embodiment 8, the following effects can be achieved.

In the functional portion 20H of the oral appliance 10H, the first insulating layer 12C is provided with the plurality of openings 12d. The plurality of sensor units 21b is arranged in regions exposed from the plurality of openings 12d. With such a configuration, the contact state of the plurality of sensor units 21b with respect to the measurement site 2 can be stabilized. In addition, the plurality of sensor units 21b can be arranged closer to the measurement site 2. Accordingly, the detection sensitivity of the plurality of sensor units 21b can be improved.

In the plurality of openings 12d, two or more adjacent sensor units 21b among the plurality of sensor units 21b are arranged away from each other with a space S1. With such a configuration, for example, even when the saliva layer 3 is present on the surface of the measurement site 2, it is possible to stabilize the measurement values acquired by the plurality of sensor units 21b. That is, it is possible to suppress variations in the measurement values acquired by the plurality of sensor units 21b.

Further, in a case where the functional portion 20H has flexibility, when the functional portion 20H is brought into contact with the measurement site 2, the functional portion 20H is deformed. Also in such a configuration, since the gap between the plurality of sensor units 21b and the measurement site 2 can be reduced, it is possible to perform detection with higher accuracy.

In addition, by forming the opening 12d in a slit shape, the measurement site 2 can be suppressed from entering the opening 12d. This makes it easy to fill the space S1 formed by the opening 12d with the saliva layer 3. As such, it is possible to further suppress variations in measurement values due to the plurality of sensor units 21b.

Note that in Embodiment 8, an example in which the plurality of openings 12d is provided in the first insulating layer 12C has been described, but the exemplary aspects of the present invention are not limited thereto. In addition, the first insulating layer 12C only needs to be provided with the one or the plurality of openings 12d.

In Embodiment 8, an example in which the opening 12d is formed in a slit shape has been described, but the exemplary aspects of the present invention are not limited thereto. For example, the opening 12d may be formed in an elliptical shape, a triangular shape, a quadrangular shape, a circular shape, or the like when viewed from the Z direction.

In Embodiment 8, an example in which two sensor units 21b are arranged on the regions exposed from the opening 12d has been described, but the present invention is not limited thereto. One or the plurality of sensor units 21 may be arranged in the region exposed from the opening 12d.

In Embodiment 8, an example in which two adjacent sensor units 21 are arranged away from each other with the space S1 in the opening 12d has been described, but the present invention is not limited thereto. For example, in the opening 12d, two or more sensor units 21b may be arranged away from each other with an insulator interposed therebetween.

In Embodiment 8, an example in which a part of surfaces (e.g., sensor surface) of the plurality of sensor units 21b is covered with the first insulating layer 12C has been described, but the present invention is not limited thereto. For example, the surfaces of the plurality of sensor units 21 need not be covered with the first insulating layer 12C.

Although an example in which the plurality of sensor units 21b is the impedance measurement sensor or the resistance sensor has been described in Embodiment 8, the present invention is not limited thereto. In addition, an example in which the plurality of sensor units 21b is electrodes having a quadrangular shape when viewed from the Z direction has been described, but the exemplary aspects of the present invention are not limited thereto.

In Embodiment 8, an example in which the functional portion 20H includes the plurality of sensor units 21b has been described, but the present invention is not limited thereto. For example, the functional portion 20H may have one or the plurality of energy irradiation units.

In Embodiment 8, an example in which the sensor unit 21b is the impedance measurement sensor or the resistance sensor and has electrodes has been described, but the present invention is not limited thereto. For example, the sensor unit 21b may be any other sensor having electrodes. Alternatively, the sensor unit 21b may be a sensor having no electrodes.

(Modification 4)

Figure 30A:
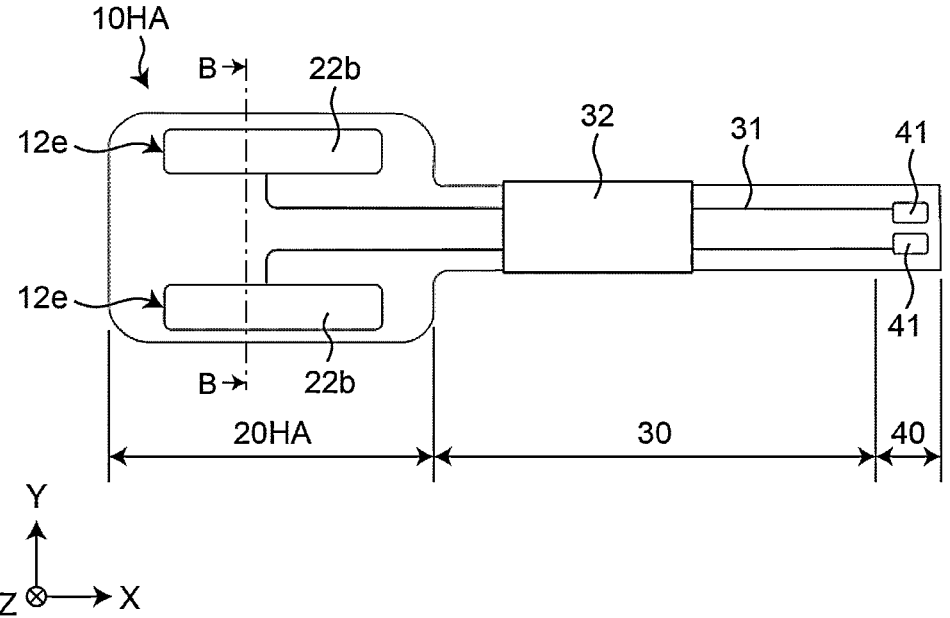
FIG. 30A is a schematic view illustrating an oral appliance of Modification 4.
Figure 30B:
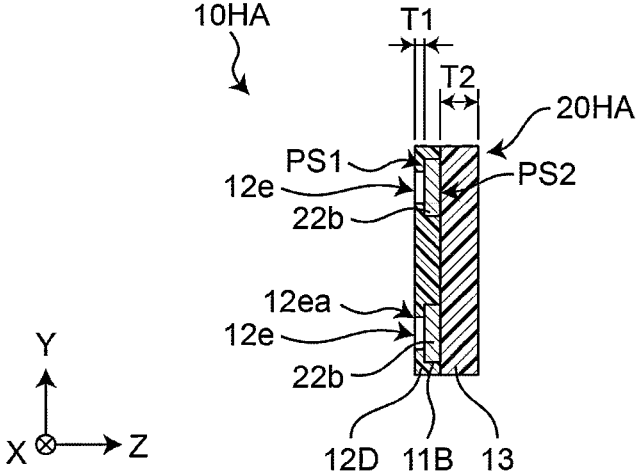
FIG. 30B is a schematic cross-sectional view of the oral appliance of Modification 4 of FIG. 30A.

FIG. 30A is a schematic view illustrating an oral appliance 10HA of Modification 4. FIG. 30B is a schematic cross-sectional view of the oral appliance 10HA of Modification 4 of FIG. 30A. The oral appliance 10HA illustrated in FIG. 30A and FIG. 30B is used as a high frequency therapeutic device. A functional portion 20HA includes a plurality of energy irradiation units 22b.

In the oral appliance 10HA, a first insulating layer 12D is provided with a plurality of openings 12e. The plurality of energy irradiation units 22b of the functional portion 20HA is respectively exposed from the plurality of openings 12e.

In Modification 4, two openings 12e are provided in the first insulating layer 12D. One energy irradiation unit 22b is arranged in each of the regions exposed from the two openings 12e.

In Modification 4, the opening 12e is formed in a rectangular shape having a longitudinal direction in the X direction. In other words, the opening 12e is formed in a slit shape extending in the X direction. In addition, the two openings 12e are provided side by side in the Y direction.

In Modification 4, the plurality of energy irradiation units 22b includes electrodes. The electrode is formed of a plate-shaped conductive material. The electrode has, for example, a rectangular shape extending in the X direction when viewed from the Z direction. The material forming the electrodes is the same as that of the electrodes of the sensor unit 21 of Embodiment 8. A high frequency current is supplied to the plurality of electrodes. The supply of the high frequency current is controlled by the body device 50.

Also in the oral appliance 10HA, by making the thickness T1 of the first insulating layer 12D smaller than the thickness T2 of the second insulating layer 13, it is possible to reduce a step 12ea between electrode surfaces of the plurality of energy irradiation units 22b and the surface of a first insulating layer 12D. With such a configuration, the contact state of the plurality of energy irradiation units 22b can be stabilized with respect to the measurement site 2. In addition, the plurality of energy irradiation units 22b can be arranged closer to the measurement site 2. Accordingly, it is possible to improve irradiation efficiency of the plurality of energy irradiation units 22b.

Note that in Modification 4, an example in which the oral appliance 10HA is a high frequency therapeutic device has been described, but the present invention is not limited thereto. The oral appliance 10HA may be a low frequency therapeutic device. In this case, a low frequency current is supplied between the plurality of electrodes.

Embodiment 9

An oral appliance according to Embodiment 9 of an exemplary aspect will be described. Note that in Embodiment 9, differences from Embodiment 1 will be mainly described. In Embodiment 9, configurations identical or equivalent to those in Embodiment 1 are denoted by the same reference numerals to be described. Further, in Embodiment 9, the description overlapping with Embodiment 1 will be omitted.

Figure 31:
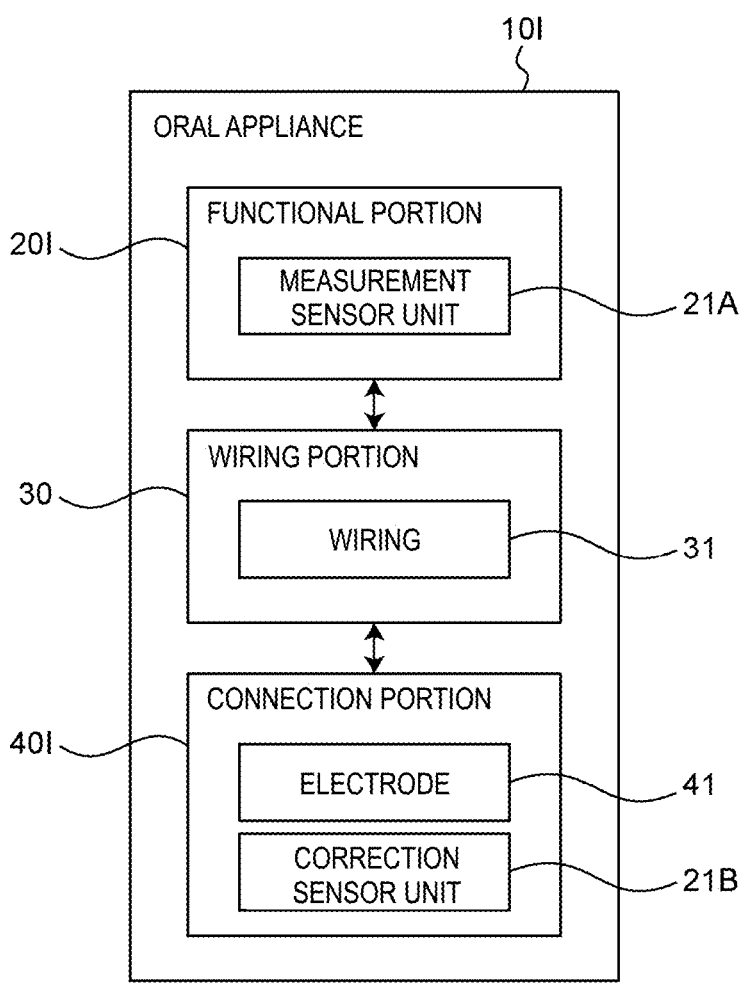
FIG. 31 is a block diagram illustrating a main configuration of an example of an oral appliance of Embodiment 9 according to an exemplary aspect.
Figure 32:
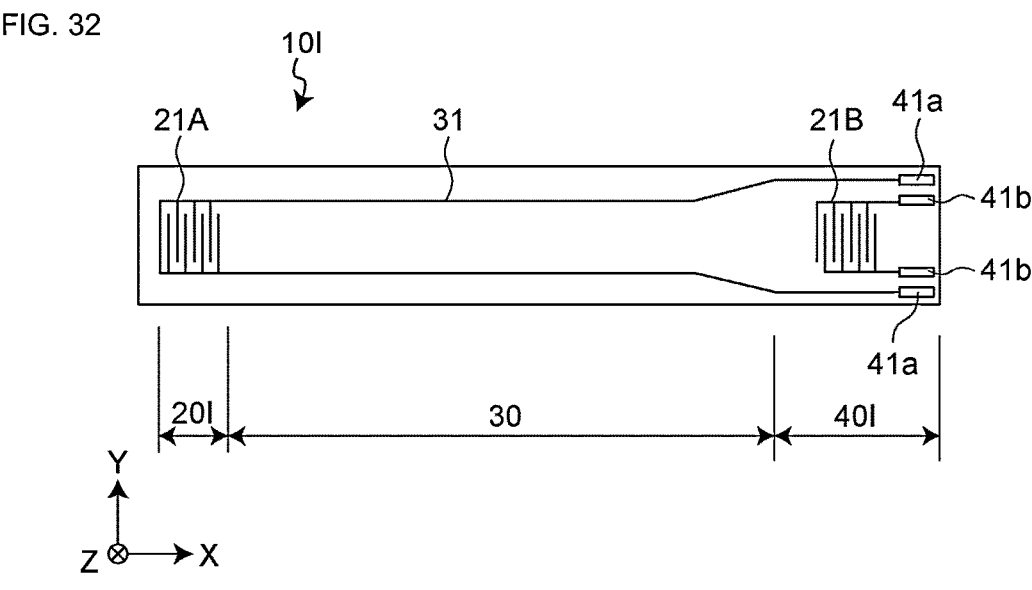
FIG. 32 is a schematic view illustrating an example of the oral appliance of Embodiment 9 according to an exemplary aspect.
Figure 33:
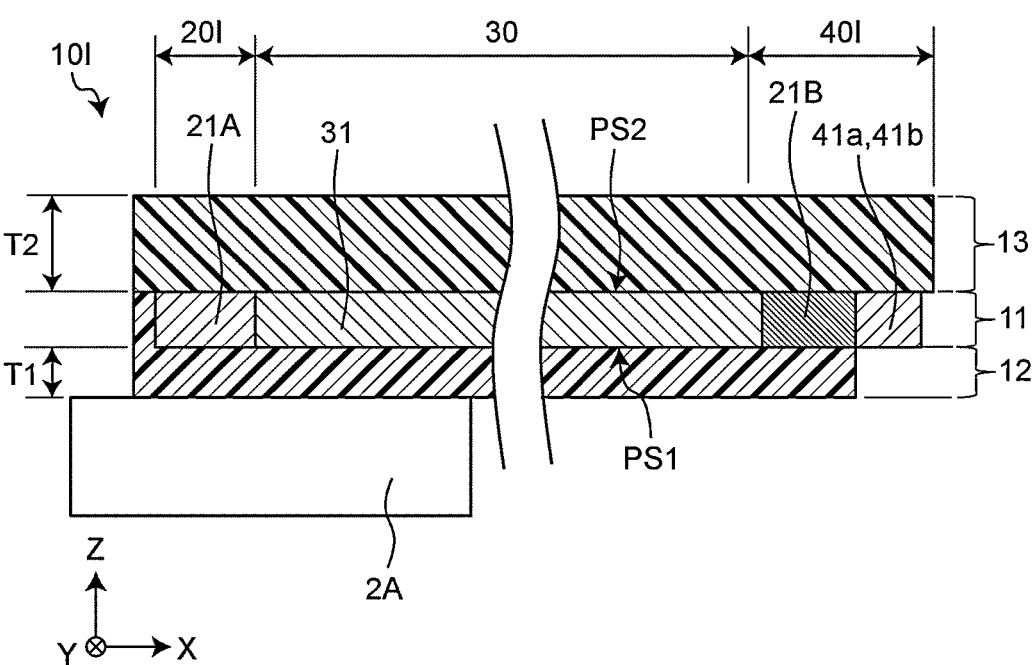
FIG. 33 is a schematic cross-sectional view illustrating an example of the oral appliance of Embodiment 9 according to an exemplary aspect in an enlarged manner.

An example of the oral appliance of Embodiment 9 will be described with reference to FIG. 31 to FIG. 33. FIG. 31 is a block diagram that illustrates an example of an oral appliance 10I of Embodiment 9 in an enlarged manner. FIG. 32 is a schematic view illustrating an example of the oral appliance 10I of Embodiment 9 according to the present invention. FIG. 33 is a schematic cross-sectional view illustrating an example of the oral appliance 10I of Embodiment 9 according to the present invention in an enlarged manner.

Embodiment 9 is different from Embodiment 1 in that a correction sensor unit 21B is arranged in a connection portion 40I.

As illustrated in FIG. 31 to FIG. 33, the oral appliance 10I includes a measurement sensor unit 21A and the correction sensor unit 21B. In Embodiment 9, the measurement sensor unit 21A is similar to the sensor unit 21 of Embodiment 1.

<Correction Sensor Unit>

The correction sensor unit 21B is arranged at a position different from that of the measurement sensor unit 21A, and acquires correction information for correcting information acquired by the measurement sensor unit 21A. The correction information is information outside the oral cavity.

The correction sensor unit 21B has the same configuration as the measurement sensor unit 21A. In Embodiment 9, the measurement sensor unit 21A is an electrostatic capacity sensor, and the correction sensor unit 21B is an electrostatic capacity sensor similar to the measurement sensor unit 21A. While the measurement sensor unit 21A measures the electrostatic capacity of a measurement site 2A in the oral cavity, the correction sensor unit 21B measures the electrostatic capacity in the atmosphere outside the oral cavity.

While the measurement sensor unit 21A is arranged in a functional portion 20I in the wiring layer 11, the correction sensor unit 21B is arranged in at least one of the wiring portion 30 and the connection portion 40I in the wiring layer 11. For example, the correction sensor unit 21B may be arranged in the wiring portion 30, the connection portion 40I, or a portion over the wiring portion 30 and the connection portion 40I in the wiring layer 11. In Embodiment 9, the correction sensor unit 21B is arranged in the connection portion 40I in the wiring layer 11. For this reason, when the oral appliance 10I is used, the measurement sensor unit 21A is arranged inside the oral cavity, while the correction sensor unit 21B is arranged outside the oral cavity.

Two electrodes 41a connected to the measurement sensor unit 21A and two electrodes 41b connected to the correction sensor unit 21B are arranged on the connection portion 40I of the oral appliance 10I. When the oral appliance 10I is attached to the body device 50, the plurality of electrodes 41a and 41b is electrically connected to the plurality of connection terminals 71 of the body device 50.

The body device 50 acquires measurement information acquired by the measurement sensor unit 21A and correction information acquired by the correction sensor unit 21B in a state of being electrically connected to the oral appliance 10I. The body device 50 is configured to correct the measurement information acquired by the measurement sensor unit 21A based on the correction information acquired by the correction sensor unit 21B. In Embodiment 9, the body device 50 corrects the electrostatic capacity acquired by the measurement sensor unit 21A based on the electrostatic capacity acquired by the correction sensor unit 21B. The correction processing may be performed by the calculation unit 63, for example. Alternatively, the body device 50 may further include a correction processing unit that performs the correction processing.

[Effects]

According to the oral appliance 10I according to Embodiment 9, the following effects can be achieved.

The oral appliance 10I includes the correction sensor unit 21B that is arranged at a position different from the measurement sensor unit 21A and acquires correction information for correcting information acquired by the measurement sensor unit 21A. With such a configuration, it is possible to acquire correction information for correcting information acquired by the measurement sensor unit 21A. Since there are individual variations in the performances of the oral appliance 10I, correction is effective for suppressing the variations. In the oral appliance 10I, since the correction information can be acquired at a position different from the measurement sensor unit 21A, it is useful for correcting the information acquired by the measurement sensor unit 21A.

The correction sensor unit 21B is arranged in at least one of the wiring portion 30 and the connection portion 40I in the wiring layer 11. With such a configuration, when the oral appliance 10I is used, the correction sensor unit 21B can be arranged outside the oral cavity. Thus, the information outside the oral cavity can be acquired as the correction information.

Note that although an example in which the oral appliance 10I includes one measurement sensor unit 21A has been described in Embodiment 9, the present invention is not limited thereto. The oral appliance 10I only needs to have one or a plurality of the measurement sensor units 21A.

Although an example in which the oral appliance 10I includes one correction sensor unit 21B has been described in Embodiment 9, the exemplary aspects of the present invention are not limited thereto. The oral appliance 10I only needs to have one or a plurality of the correction sensor units 21B.

Although an example in which the measurement sensor unit 21A and the correction sensor unit 21B are an electrostatic capacity sensor has been described in Embodiment 9, the present invention is not limited thereto. Similar to Embodiment 1, various sensors can be used as the measurement sensor unit 21A and the correction sensor unit 21B.

In Embodiment 9, an example in which the body device 50 performs the correction processing has been described, but the exemplary aspects of the present invention are not limited thereto. For example, the oral appliance 10I may perform the correction processing. For example, the oral appliance 10I may include a correction processing circuit that performs correction processing.

In Embodiment 9, an example in which the connection portion 40I includes four electrodes 41a and 41b has been described, but the exemplary aspects of the present invention are not limited thereto. For example, in a case where the measurement sensor unit 21A and the correction sensor unit 21B are potential sensors, either one of the positive electrode or the negative electrode may be shared by the measurement sensor unit 21A and the correction sensor unit 21B.

(Modification 5)

Figure 34:
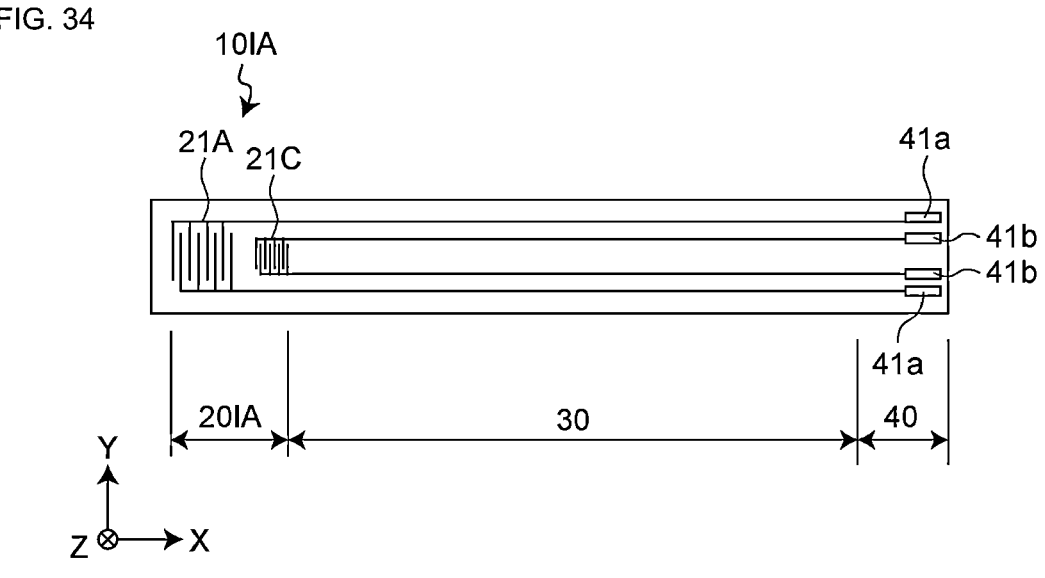
FIG. 34 is a schematic view illustrating an oral appliance of Modification 5.
Figure 35:
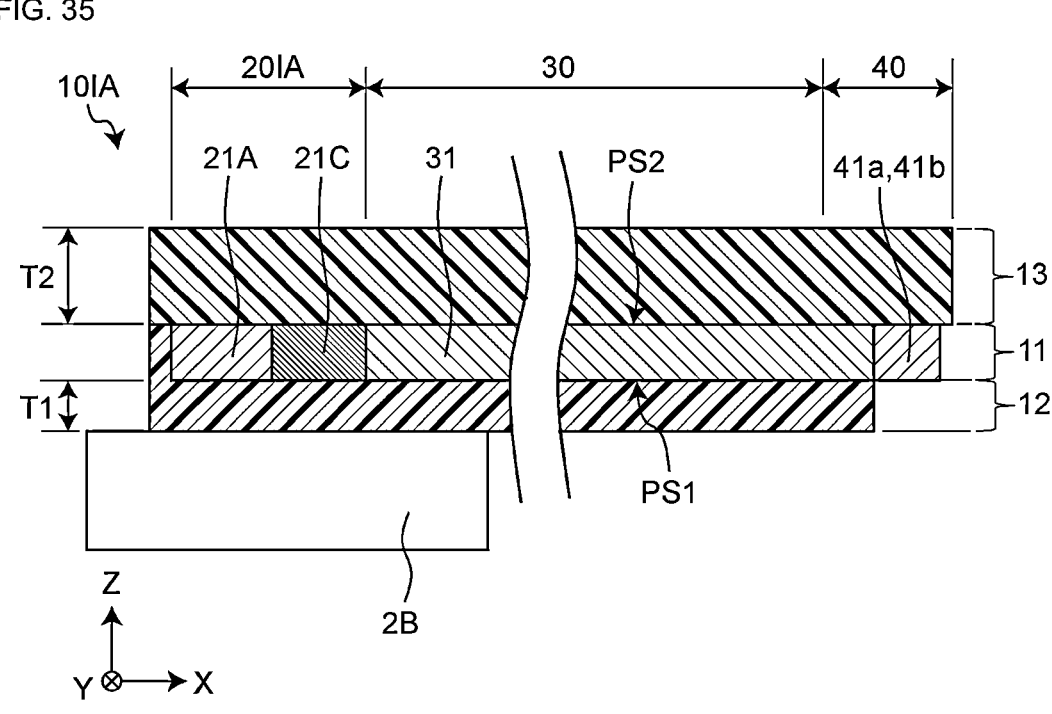
FIG. 35 is a schematic cross-sectional view of the oral appliance of Modification 5 of FIG. 34.

FIG. 34 is a schematic view illustrating an oral appliance 10IA of Modification 5. FIG. 35 is a schematic cross-sectional view of the oral appliance 10IA of Modification 5 of FIG. 34. As illustrated in FIG. 34 and FIG. 35, in the oral appliance 10IA, the correction sensor unit 21C is arranged side by side in the functional portion 20IA in the wiring layer 11. In addition, the correction sensor unit 21C is configured to acquire information in the oral cavity with a detection sensitivity different from that of the measurement sensor unit 21A. This configuration suppresses variations in measurement values due to variations in the thickness T1 of the first insulating layer 12.

The correction sensor unit 21C is arranged at a position not overlapping with the measurement sensor unit 21A in the Z direction. To be specific, the correction sensor unit 21C is arranged side by side with the measurement sensor unit 21A along the first insulating layer 12 in the wiring layer 11 of the functional portion 20IA. In Modification 5, the measurement sensor unit 21A and the correction sensor unit 21C are arranged adjacent to each other in the X direction. Note that the correction sensor unit 21C and the measurement sensor unit 21A are not adjacent to each other in some case but may be separated from each other.

As illustrated in FIG. 35, the oral appliance 10IA brings the functional portion 20IA into contact with a measurement site 2B in the oral cavity. The measurement site 2B is, for example, the tongue portion of a patient or user. The measurement sensor unit 21A and the correction sensor unit 21C acquire information on the measurement site 2B in the oral cavity. The correction sensor unit 21C is configured to acquire information in the oral cavity with a detection sensitivity different from that of the measurement sensor unit 21A. Therefore, information (e.g., measurement values) acquired by the measurement sensor unit 21A and the correction sensor unit 21C are different from each other.

Figure 36:
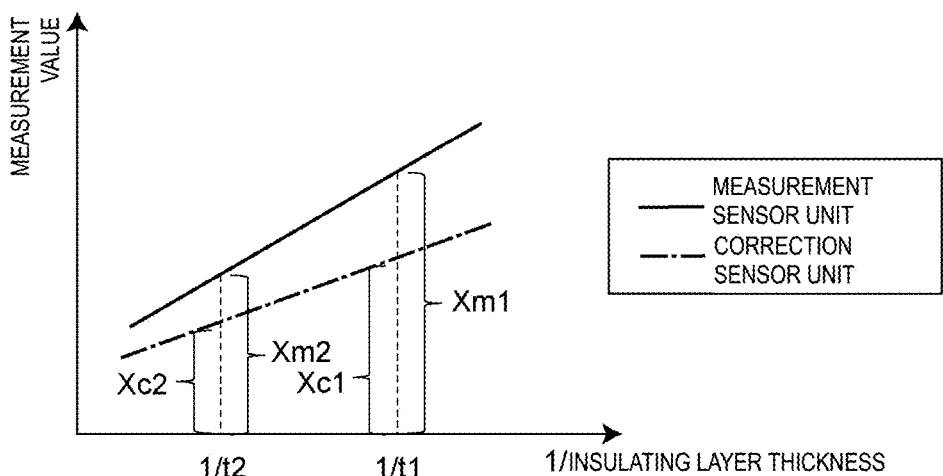
FIG. 36 is a graph illustrating an example of a relationship between measurement values of a measurement sensor unit and a correction sensor unit.

FIG. 36 is a graph illustrating an example of a relationship between measurement values of the measurement sensor unit 21A and the correction sensor unit 21C. As illustrated in FIG. 36, when the thickness of the first insulating layer 12 is t1, the measurement value of the measurement sensor unit 21A is Xm1, and the measurement value of the correction sensor unit 21C is Xc1. When the thickness of the first insulating layer 12 is t2, the measurement value of the measurement sensor unit 21A is Xm2, and the measurement value of the correction sensor unit 21C is Xc2. Note that $t1<t2$ is satisfied. In this case, the correction sensor unit 21C is configured to satisfy $(Xm2/Xc2) \neq (Xm1/Xc1)$. Thus, by calculating the ratio $(Xm/Xc)$ between the measurement value Xm of the measurement sensor unit 21A and the measurement value Xc of the correction sensor unit 21C, the thickness T1 of the first insulating layer 12 can be estimated and corrected.

For example, in the case where the correction sensor unit 21C is an electrostatic capacity sensor having comb electrodes, the detection sensitivity of the correction sensor unit 21C can be changed by changing the line interval and/or line width of the comb electrodes.

As described above, in the oral appliance 10IA, the thickness T1 of the first insulating layer 12 can be estimated and corrected by using the correction sensor unit 21C having a detection sensitivity different from that of the measurement sensor unit 21A. This makes it possible to suppress variations in measurement values due to variations in the thickness T1 of the first insulating layer 12.

In general, it is noted that although the present invention has been fully described in connection with the preferred embodiments with reference to the accompanying drawings, various changes and modifications will become apparent to those skilled in the art.

The oral appliance of the present invention can be applied to, for example, a disposable type oral device or the like.

REFERENCE SIGNS LIST 1A, 1B, 1C, 1D, 1E, 1F ORAL DEVICE
2, 2A, 2B MEASUREMENT SITE
3 SALIVA LAYER
10, 10A, 10AA, 10B, 10C, 10D, 10E, 10EA, 10F, 10G, 10H, 10HA, 10I, 10IA ORAL APPLIANCE
11 WIRING LAYER
12 12A, 12B, 12C, 12D FIRST INSULATING LAYER
12a INSULATOR
12b RESIN FILM

12*c* HOLE
12*d*, 12*e* OPENING
12*da*, 12*ea* STEP
13 SECOND INSULATING LAYER
14 FIRST SHIELD LAYER
15 SECOND SHIELD LAYER
16 THIRD INSULATING LAYER
17 FOURTH INSULATING LAYER
18 HEAT INSULATING MATERIAL
20, 20E, 20EA, 20H, 20HA, 20I, 20IA FUNCTIONAL PORTION
21 SENSOR UNIT
21A MEASUREMENT SENSOR UNIT
21B, 21C CORRECTION SENSOR UNIT
21*a* SENSOR SURFACE
22, 22*a*, 22*b* ENERGY IRRADIATION UNIT
30, 30B WIRING PORTION
31 WIRING
32 PROTECTIVE LAYER
40, 40A, 40AA, 40D, 40E, 40F, 40I CONNECTION PORTION
41, 41*a*, 41*b* ELECTRODE (ELECTRICAL CONNECTION PORTION)
42 MOUNTING HOLE
43 RFID TAG (ELECTRICAL CONNECTION PORTION)
44 ANTENNA
45 IC CHIP
46 SECOND SENSOR UNIT
50, 50C, 50E, 50F ORAL BODY DEVICE
60, 60C BODY PORTION
61, 61C GRIP PORTION
62 CONTROL UNIT
63 CALCULATION UNIT
70, 70A, 70C, 70F, 70G ATTACHMENT/DETACHMENT OPERATION UNIT
71 CONNECTION TERMINAL (ELECTRICAL CONNECTION CONDUCTOR)
72 ARRANGEMENT SURFACE
72*a* POSITIONING MEMBER
72*aa* BOTTOM SURFACE
72*ab*, 72*ac* INCLINED SURFACE
73, 73A, 73C PRESSING MEMBER
73*a* PROTRUSION
74 ROTATION SHAFT
78 ANTENNA (ELECTRICAL CONNECTION CONDUCTOR)
79 COLUMNAR MEMBER
80 GUARD
90 DISPLAY UNIT
91 INPUT UNIT

The invention claimed is:

1. A sheet-shaped oral appliance detachably attached to an oral body device, comprising:
a functional portion that includes either at least one sensor unit configured to acquire information in an oral cavity or at least one energy irradiation unit configured to radiate energy into the oral cavity;
a connection portion having an electrical connection portion; and
a wiring portion including a wiring that connects the at least one sensor unit or the at least one energy irradiation unit to the electrical connection portion,
wherein the functional portion, the connection portion, and the wiring portion comprise:

a wiring layer having a first main surface on a first plane and a second main surface on a second plane and below the first main surface; and
a plurality of insulating layers including a first insulating layer disposed on and above the first main surface of the wiring layer and a second insulating layer disposed on and below the second main surface of the wiring layer, and wherein the first insulating layer has a thickness that is smaller than a thickness of the second insulating layer in the functional portion.

2. The oral appliance according to claim 1, wherein the wiring layer and the plurality of insulating layers are stacked.

3. The oral appliance according to claim 1, wherein the wiring portion has a thickness that is larger than a thickness of the functional portion.

4. The oral appliance according to claim 1, wherein the wiring portion has at least one shield layer disposed on the plurality of insulating layers.

5. The oral appliance according to claim 1, wherein the wiring portion has a protective layer disposed on an outer periphery of the wiring portion.

6. The oral appliance according to claim 1, wherein the at least one sensor unit has a sensor surface configured to acquire information on a measurement site in the oral cavity, with the sensor surface being disposed on the first main surface of the wiring layer.

7. The oral appliance according to claim 1, wherein the at least one energy irradiation unit is disposed on the first main surface of the wiring layer.

8. The oral appliance according to claim 1, wherein the functional portion is flexible.

9. The oral appliance according to claim 1,
wherein, in the functional portion, the first insulating layer comprises at least one opening, and
wherein the at least one sensor unit or the at least one energy irradiation unit is disposed in a region that is exposed from the at least one opening.

10. The oral appliance according to claim 9, wherein the at least one sensor unit comprises two or more adjacent sensor units that are arranged away from each other with a space in the at least one opening.

11. The oral appliance according to claim 1, further comprising a correction sensor unit that is disposed at a position different from the at least one sensor unit and that is configured to acquire correction information for correcting information acquired by the at least one sensor unit.

12. The oral appliance according to claim 11, wherein the correction sensor unit is disposed in at least one of the wiring portion and the connection portion in the wiring layer.

13. The oral appliance according to claim 11, wherein the correction sensor unit is disposed side by side with the at least one sensor unit along the first insulating layer in the wiring layer of the functional portion, and is configured to acquire information in the oral cavity with a detection sensitivity different from a detection sensitivity of the at least one sensor unit.

14. The oral appliance according to claim 1, wherein the electrical connection portion is at least one electrode that is exposed from at least one of the first insulating layer and the second insulating layer.

15. The oral appliance according to claim 1, wherein the electrical connection portion is an RFID tag.

16. The oral appliance according to claim 1, wherein the oral appliance is configured in a bag shape in which the first main surface of the wiring layer faces outward and the second main surface of the wiring layer faces inward.

17. The oral appliance according to claim 1, wherein the wiring portion is disposed in a planar direction between the functional portion and the connection portion.

18. The oral appliance according to claim 17, wherein the at least one sensor unit of the functional portion is disposed between the first and second insulating layers relative to a direction perpendicular to the planar direction.

19. An oral appliance comprising:

a functional portion having a sensor unit configured to acquire information in an oral cavity and an irradiation unit configured to radiate energy into the oral cavity;

a connection portion having an electrical connection portion; and a wiring layer that connects at least one of the sensor unit and the energy irradiation unit to the electrical connection portion, with the wiring layer having first main surface on a first plane and a second main surface on a second plane and below the first main surface;

a first insulating layer disposed on and above the first main surface of the wiring layer; and a second insulating layer disposed on and below the second main surface of the wiring layer, wherein the functional portion is disposed between the first and second insulating layers and the first insulating layer has a thickness that is smaller than a thickness of the second insulating layer where the respective insulating layers cover the functional portion.

20. The oral appliance according to claim 19, wherein, in the functional portion, the first insulating layer comprises at least one opening, and wherein at least one of the sensor unit and the energy irradiation unit is disposed in a region that is exposed from the at least one opening.

\* \* \* \* \*